United States Patent
Sugiura

(10) Patent No.: US 8,571,288 B2
(45) Date of Patent: Oct. 29, 2013

(54) IMAGE DISPLAY APPARATUS AND MAGNETIC RESONANCE IMAGING APPARATUS

(75) Inventor: Satoshi Sugiura, Otawara (JP)

(73) Assignees: Kabushiki Kaisha Toshiba, Minato-Ku, Tokyo; Toshiba Medical Systems Corporation, Otawara-Shi, Tochigi (JP)

( * ) Notice: Subject to any disclaimer, the term of this patent is extended or adjusted under 35 U.S.C. 154(b) by 990 days.

(21) Appl. No.: 12/326,304

(22) Filed: Dec. 2, 2008

(65) Prior Publication Data

US 2009/0148020 A1   Jun. 11, 2009

(30) Foreign Application Priority Data

Dec. 7, 2007 (JP) ................................. 2007-317698
Oct. 22, 2008 (JP) ................................. 2008-272449

(51) Int. Cl.
*G06K 9/00* (2006.01)

(52) U.S. Cl.
USPC ........................... 382/131; 345/530; 600/413

(58) Field of Classification Search
USPC ............................ 382/131; 345/530; 600/413
See application file for complete search history.

(56) References Cited

U.S. PATENT DOCUMENTS

| | | | |
|---|---|---|---|
| 5,038,786 A | 8/1991 | Kojima | |
| 6,484,048 B1 * | 11/2002 | Hoshino et al. | 600/410 |
| 2004/0087853 A1 * | 5/2004 | Fujisawa | 600/425 |
| 2004/0181146 A1 * | 9/2004 | Yarnykh et al. | 600/419 |
| 2006/0050943 A1 * | 3/2006 | Ozaki et al. | 382/131 |
| 2006/0208730 A1 * | 9/2006 | Kozerke et al. | 324/307 |
| 2006/0241412 A1 * | 10/2006 | Rinck et al. | 600/431 |
| 2006/0280349 A1 * | 12/2006 | Hildebrand et al. | 382/128 |
| 2007/0229500 A1 * | 10/2007 | Engel et al. | 345/422 |
| 2008/0069417 A1 * | 3/2008 | Kimura | 382/131 |
| 2008/0071167 A1 * | 3/2008 | Ikedo et al. | 600/419 |
| 2008/0317310 A1 * | 12/2008 | Suresh et al. | 382/130 |
| 2009/0148020 A1 * | 6/2009 | Sugiura | 382/131 |

FOREIGN PATENT DOCUMENTS

| | | |
|---|---|---|
| JP | 10-124649 | 5/1998 |
| JP | 2003-325469 | 11/2003 |
| JP | 2008-167838 | 7/2008 |

* cited by examiner

*Primary Examiner* — Hrayr A Sayadian
(74) *Attorney, Agent, or Firm* — Nixon & Vanderhye PC

(57) ABSTRACT

An image display apparatus includes a storage unit that stores a plurality of image data with respect to a scan area of a subject; an analysis processing unit that obtains a plurality of analysis results by performing a predetermined analysis processing on a plurality of image data stored in the storage unit; a display unit that displays image data stored in the storage unit along with analysis results obtained by the analysis processing unit; and an image-display control unit that performs control such that image data corresponding to a specified analysis result is to be displayed on the display unit, when at least one analysis result is specified from among the analysis results displayed by the display unit.

25 Claims, 17 Drawing Sheets

IMAGE DISPLAY APPARATUS AND MAGNETIC RESONANCE IMAGING APPARATUS

CROSS-REFERENCE TO RELATED APPLICATIONS

This application is based upon and claims the benefit of priority from the prior Japanese Patent Application No. 2007-317698, filed on Dec. 7, 2007, and No. 2008-272449, filed on Oct. 22, 2008; the entire contents of which are incorporated herein by reference.

BACKGROUND

1. Technical Field

The present invention relates to an image display apparatus and a magnetic resonance imaging apparatus each of which displays thereon images of various dimensions. The present invention particularly relates to an image display apparatus and a magnetic resonance imaging apparatus each of which can efficiently provide image observation by associating an image with a plurality of dimensions.

2. Description of the Related Art

Conventionally, when a diagnostic imaging apparatus, such as a Magnetic Resonance Imaging (MRI) apparatus or an X-ray Computed Tomography (CT) apparatus, displays volume data of three dimensions, there is a method of displaying an axial image, a sagittal image, and a coronal image, which are orthogonal to one another, in a manner associated with respective positional relations (for example, see JP-A H10-124649 (KOKAI)). A technology of reconstructing multiplanar images, such as an axial image, a sagittal image, and a coronal image, is called Multi Planar Reconstruction (MPR).

FIG. 17 is a schematic diagram illustrating an example of an MPR screen according to a conventional diagnostic imaging apparatus. FIG. 17 depicts an MPR screen on which images of a head that have data of three dimensions are displayed, and a coronal image, an axial image, and a sagittal image are output in a frame A on the upper left, in a frame B on the lower left, and in a frame C on the upper right, respectively.

On the MPR screen, each line Region Of Interest (ROI) displayed horizontally or vertically in the frames A, B and C indicates a slice position of a cross section output in another frame; and as an operator moves a line ROI in one of the frames, a cross-sectional image output in another frame can be changed in accordance with a position of the moved line ROI.

According to the MPR screen, as an operator arranges an ROI at an arbitrary position in the frames A, B, or C, a cross-sectional image corresponding to the position can be reconstructed and displayed in a frame D, so that the operator can easily display an arbitrary cross-sectional image when there is a large amount of image data of three dimensions obtained by an X-ray CT apparatus or an MRI apparatus.

A diagnostic imaging apparatus, such as an MRI apparatus or an X-ray CT apparatus, can collect a plurality of images of two spatial dimensions or three spatial dimensions taken at different times. For example, in a case of an MRI apparatus, dimensions other than three spatial dimensions, for example, time and chemical shift, are present depending on a data collection method, so that there are image data per time point and image data per chemical shift with respect to the same position.

However, according to the conventional method described above, an image of three spatial dimensions cannot be displayed in an associated manner with the other non-spatial dimensions. For this reason, for example, to display an image taken at a different time at the same position, the image needs to be newly selected again, or a time point needs to be input as a numerical value, so that it is difficult to operate those processes intuitively and simply.

SUMMARY OF THE EXEMPLARY EMBODIMENTS

According to one aspect of the present invention, an image display apparatus includes a storage unit that stores a plurality of image data with respect to a scan area of a subject; an analysis processing unit that obtains a plurality of analysis results by performing a predetermined analysis processing on a plurality of image data stored in the storage unit; a display unit that displays image data stored in the storage unit along with analysis results obtained by the analysis processing unit; and an image-display control unit that performs control such that image data corresponding to a specified analysis result is to be displayed on the display unit, when at least one analysis result is specified from among the analysis results displayed by the display unit.

According to another aspect of the present invention, an image display apparatus includes a storage unit that stores a plurality of image data with respect to a scan area of a subject in a manner associated with a parameter value of a scanning parameter set for a scan of the scan area; a display unit that displays image data stored in the storage unit; an input receiving unit that receives an input of a parameter value of the scanning parameter; and an image-display control unit that reads image data corresponding to the parameter value from the storage unit when the input of the parameter value is received by the input receiving unit, and causes the display unit to display the read image data.

According to still another aspect of the present invention, an image display apparatus includes a storage unit that stores image data that is reconstructed with respect to each cardiac time phase based on data collected across a plurality of heart beats; a display unit that displays image data stored in the storage unit and an electrocardiographic waveform of one heart beat; and an image-display control unit that reads image data corresponding to a specified cardiac time phase when an arbitrary cardiac time phase on the electrocardiographic waveform displayed by the display unit is specified, and causes the display unit to display the read image data.

According to still another aspect of the present invention, a magnetic resonance imaging apparatus includes a storage unit that stores image data that is reconstructed with respect to each cardiac time phase based on data collected across a plurality of heart beats; a display unit that displays image data stored in the storage unit and an electrocardiographic waveform of one heart beat; and an image-display control unit that reads image data corresponding to a specified cardiac time phase when an arbitrary cardiac time phase on the electrocardiographic waveform displayed by the display unit is specified, and causes the display unit to display the read image data.

DETAILED DESCRIPTION OF EXEMPLARY EMBODIMENTS

Exemplary embodiments of an image display apparatus and a magnetic resonance imaging apparatus according to the present invention will be explained below in detail with reference to the accompanying drawings.

First of all, a configuration of a Magnetic Resonance Imaging (MRI) apparatus according to a first embodiment of the present invention is explained below.

Figure 1:
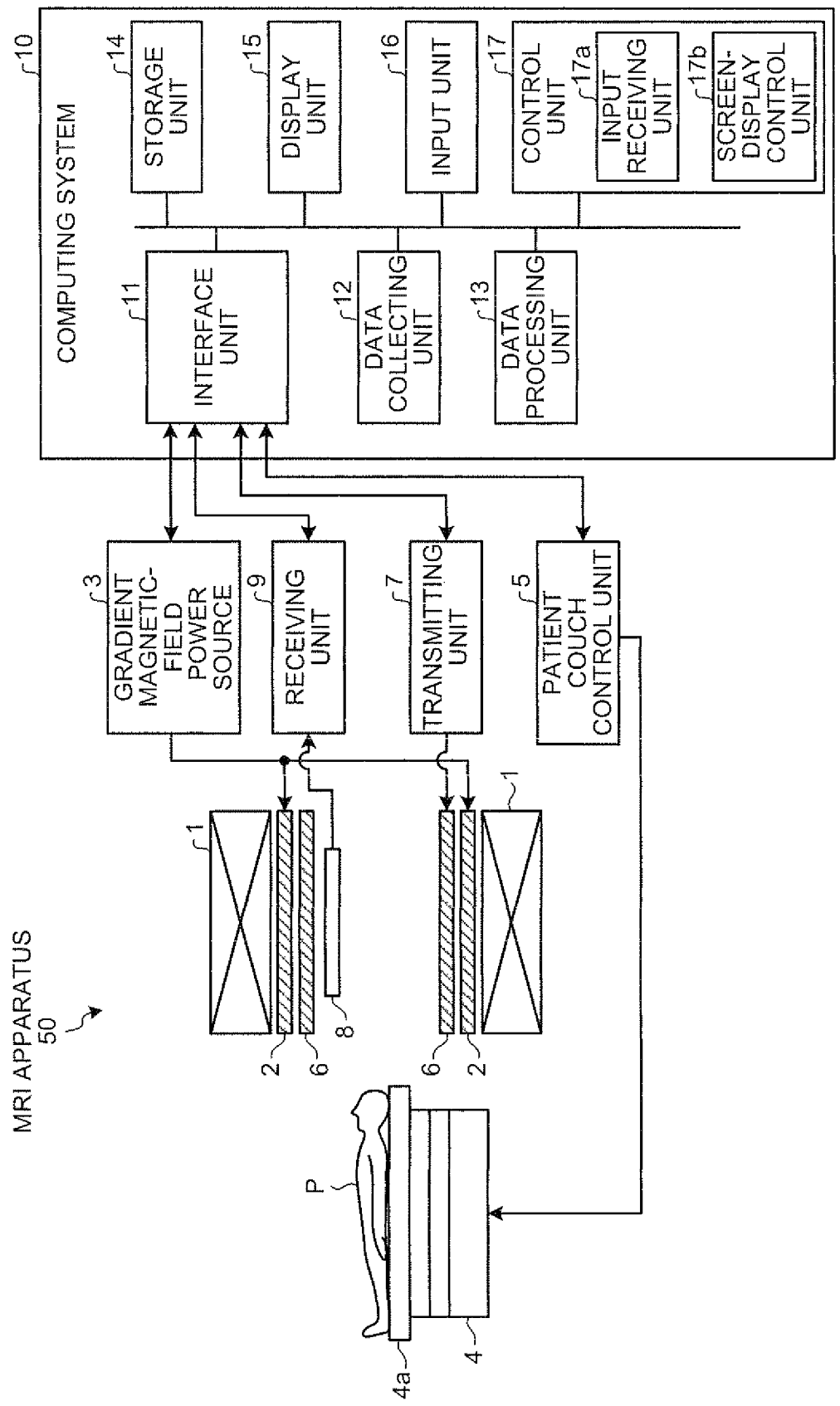
FIG. 1 is a schematic diagram illustrating a configuration of a Magnetic Resonance Imaging (MRI) apparatus according to a first embodiment of the present invention.

FIG. 1 is a schematic diagram illustrating a configuration of an MRI apparatus 50 according to the first embodiment. As shown in FIG. 1, the MRI apparatus 50 includes a static magnetic-field magnet 1, a gradient magnetic-field coil 2, a gradient magnetic-field power source 3, a patient couch 4, a patient couch control unit 5, a transmitting RF coil 6, a transmitting unit 7, a receiving Radio Frequency (RF) coil 8, a receiving unit 9, and a computing system 10.

The static magnetic-field magnet 1 is a magnet formed in a hollow cylindrical shape, and generates a uniform static magnetic field in a space its inside. For example, a permanent magnet, or a super conducting magnet is used as the static magnetic-field magnet 1.

The gradient magnetic-field coil 2 is formed in a hollow cylindrical shape, and is arranged inside the static magnetic-field magnet 1. The gradient magnetic-field coil 2 is formed of combined three coils corresponding to x, y, and z axes orthogonal to one another, and the three coils generate gradient magnetic fields along three directions of the x, y, and z axes by receiving a current supply individually from the gradient magnetic-field power source 3, which will be described later. For example, it is assumed that the z axis direction is the same direction as the static magnetic field.

The gradient magnetic fields of the x, y, and z axes generated by the gradient magnetic-field coil 2 correspond, for example, a slice-selective gradient magnetic field Gs, a phase encoding gradient magnetic field Ge, and a readout gradient magnetic field Gr, respectively. The slice selective gradient magnetic field Gs is used for arbitrarily determining a scan cross section. The phase encoding gradient magnetic field Ge is used for changing a phase of a magnetic resonance signal in accordance with a spatial position. The readout gradient magnetic field Gr is used for changing the frequency of a magnetic resonance signal in accordance with a spatial position.

The gradient magnetic-field power source 3 supplies a current to the gradient magnetic-field coil 2. The patient couch 4 is a device that includes a top plate 4a on which the subject P is to be placed. Under the control of the couch control unit 5, which will be described later, the patient couch 4 inserts the top plate 4a on which the subject P is placed, into a hole (a scanning space) of the gradient magnetic-field coil 2. Usually, the patient couch 4 is placed such that the longitudinal direction of the patient couch 4 is to be parallel to the central axis of the static magnetic-field magnet 1.

The patient couch control unit 5 controls the patient couch 4, and moves the top plate 4a in the longitudinal direction and upward and down ward by driving the patient couch 4. The transmitting RF coil 6 is arranged inside the gradient magnetic-field coil 2, and generates a high-frequency magnetic field by receiving supply of a high-frequency pulse from the transmitting unit 7.

The transmitting unit 7 includes an oscillating unit, a phase selecting unit, a frequency converting unit, an amplitude modulating unit, and a high-frequency power amplifying unit. The oscillating unit generates a high-frequency signal of a resonance frequency unique to a subject nucleus in the static magnetic field. The phase selecting unit selects a phase of the high-frequency signal. The frequency converting unit converts a frequency of the high-frequency signal output by the phase selecting unit. The amplitude modulating unit modulates amplitude of the high frequency signal output by the frequency converting unit in accordance with, for example, a sinc function. The high frequency power amplifying unit amplifies the high-frequency signal output by the amplitude modulating unit. As a result of operation performed by the above units, the transmitting unit 7 sends a high-frequency pulse corresponding to a Larmor frequency to the transmitting RF coil 6.

The receiving RF coil 8 is arranged inside the gradient magnetic-field coil 2, and receives a magnetic resonance signal irradiated from the subject P owing to an influence of the high-frequency magnetic field. The output signal received by the receiving RE coil 8 is input into the receiving unit 9. The receiving unit 9 creates magnetic resonance signal data based on the output signal from the receiving RF coil 8.

The computing system 10 performs total control of the MRI apparatus 50, data collection, and image reconstruction, and includes an interface unit 11, a data collecting unit 12, a data processing unit 13, a storage unit 14, a display unit 15, an input unit 16, and a control unit 17.

The interface unit 11 receives and outputs signals given and received between each of the above connected units and the computing system 10. The interface unit 11 is connected to the gradient magnetic-field power source 3, the patient couch control unit 5, the transmitting unit 7, the receiving RF coil 8, and the receiving unit 9, and the like.

The data collecting unit 12 collects a digital signal output by the receiving unit 9 via the interface unit 11. The data collecting unit 12 stores the collected digital signal, i.e., magnetic resonance signal data, into the storage unit 14.

The data processing unit 13 executes post-processing, i.e., reconstruction, such as Fourier transformation, on the magnetic resonance signal data stored in the storage unit 14, and creates spectrum data or image data of a desired nuclear spin in the subject P.

The storage unit 14 stores therein various data. The storage unit 14 stores therein, for example, magnetic resonance signal data collected by the data collecting unit 12, and spectrum data and image data (for example, volume data of three dimensions) created by the data processing unit 13, with respect to each patient. When storing data, the storage unit 14 stores therein image data in a manner associated with a plurality of dimensions, such as spatial three dimensions and time.

The display unit 15 displays thereon various information, such as spectrum data or image data, under the control of the control unit 17. A display device, such as a liquid crystal display, can be used as the display unit 15.

The input unit 16 receives various instructions and information input from an operator. As the input unit 16, input devices, for example, pointing devices, such as a mouse or a trackball, a selecting device, such as a mode switch, and a keyboard, can be used as required.

The control unit 17 includes a Central Processing Unit (CPU) and a memory, both of which are not shown, and totally controls the MRI apparatus 50 according to the first embodiment. For example, the control unit 17 displays on the display unit 15 a user interface for receiving various inputs, then receives an instruction from an operator, and displays an image created by the data processing unit 13 on the display unit 15. The control unit 17 includes an input receiving unit 17a and a screen-display control unit 17b as processing units related to input reception and image display.

The input receiving unit 17a causes the display unit 15 to display an image of a specific dimension, and receives input information about other dimensions different from the specific dimension. Specifically, when receiving an instruction to display image data from the operator via the input unit 16, the input receiving unit 17a displays an image of a specific dimension, and outputs on the display unit 15 an image viewing screen for receiving input information about other dimensions from the operator.

Figure 2:
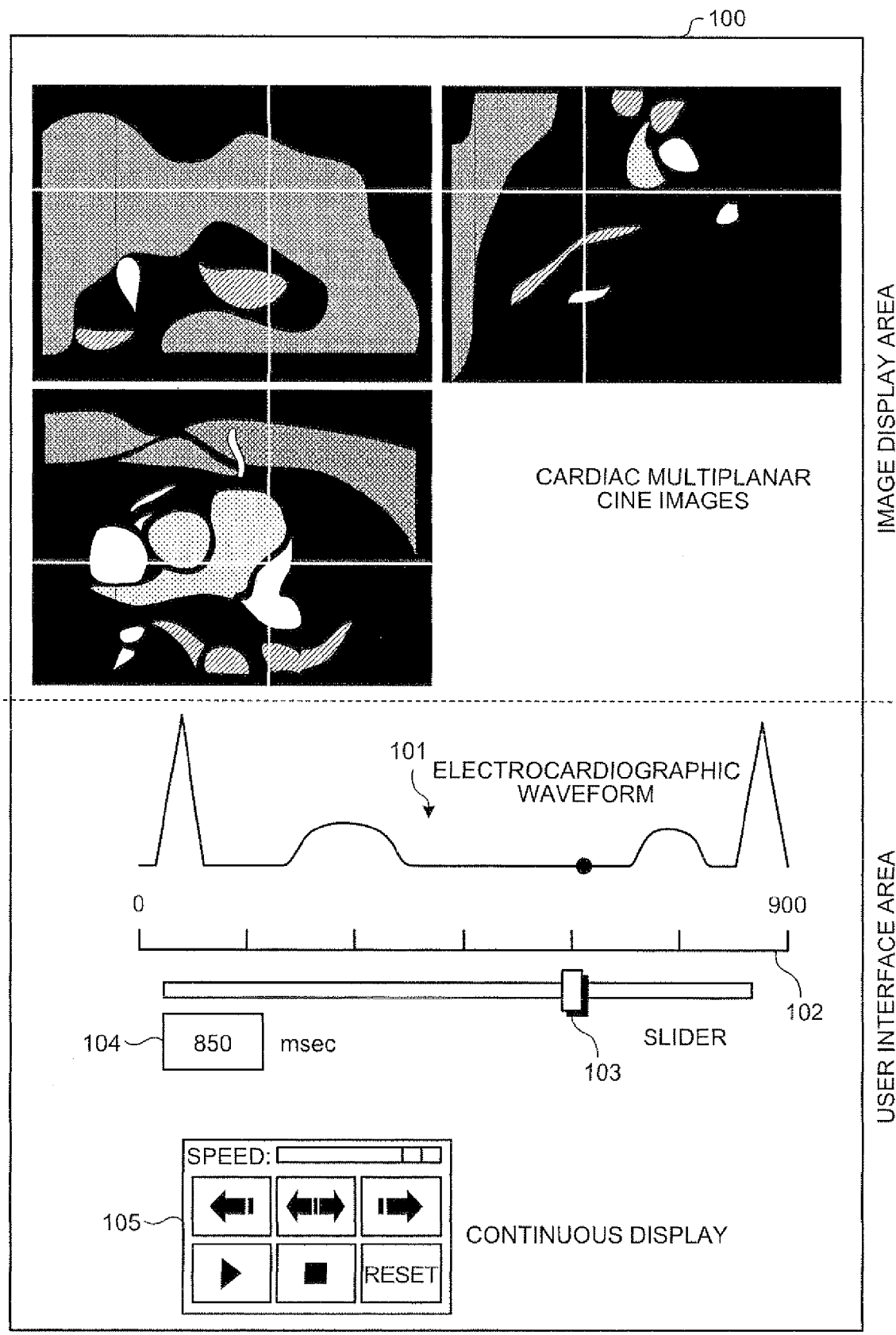
FIG. 2 is a schematic diagram illustrating an example of an image viewing screen displayed by an input receiving unit.

FIG. 2 is a schematic diagram that depicts an example of an image viewing screen displayed by the input receiving unit 17a. As shown in FIG. 2, for example, an image viewing screen 100 includes an image display area for displaying images of spatial three dimensions, and a user interface area for receiving input information about cardiac time phase.

In the image display area, for example, cardiac cine MRI images of three spatial dimensions obtained by electrocardiogram (ECG) gated imaging (or pulse-wave synchronized imaging) are displayed (the cardiac multiplanar cine images shown in FIG. 2). Specifically, in the image display area, a cine image of a coronal image is displayed on the upper left; a cine image of an axial image is displayed on the lower left; and a cine image of a sagittal image is displayed on the upper right. Image data that is a base of each of the cine images is collected in each of cardiac time phases in a cardiac cycle, and a plurality of image data in different phases is stored in the storage unit 14 in addition to the displayed images.

On the other hand, in the user interface area, for example, information associated with spatial information and temporal information is displayed. Specifically, in the user interface area, for example, an electrocardiographic waveform 101, a scale 102, a slider (slide bar) 103, an input box 104, and a continuous display panel 105 are displayed. The electrocardiographic waveform 101 is an electrocardiographic waveform (or a pattern of pulse wave) actually captured from the subject P, or a simulation diagram that depicts one cardiac cycle. The scale 102 indicates cardiac time phases. The slider 103 is for the operator to specify a phase that the operator desires to observe. The input box 104 is for the operator to input directly a time point (msec) that indicates a phase. The continuous display panel 105 is for the operator to operate continuous display of images.

As the electrocardiographic waveform 101, an electrocardiographic waveform can be described with average R—R intervals of the subject P (900 msec in FIG. 2), or a typical electrocardiographic waveform of the subject P that is collected during an actual scan.

When the input receiving unit 17a receives input information about another dimension, the screen-display control unit 17b reads image data corresponding to the dimension of the received information from image data stored by the storage unit 14, and displays an image of the specific dimension based on the read image data.

Specifically, when the input receiving unit 17a receives input information about another dimension, the screen-display control unit 17b, by controlling the data processing unit 13, reads image data corresponding to the dimension of the received information, creates various images by performing on the read image data post-processing, such as MPR and a cardiac function analysis, and displays the created images on the display unit 15.

For example, in a case of using the image viewing screen 100 shown in FIG. 2, when a phase is specified by operation of the slider 103 or input of a numerical value into the input box 104, the screen-display control unit 17b reads image data corresponding to the specified phase from the storage unit 14, creates cine images of a coronal image, an axial image, and a sagittal image based on the read image data, and displays the created images in the image display area. When displaying the images, the screen-display control unit 17b displays a black point indicated on the electrocardiographic waveform 101 and a numerical value inside the rectangle in a linked manner with a time point set by the slider 103.

Figure 3:
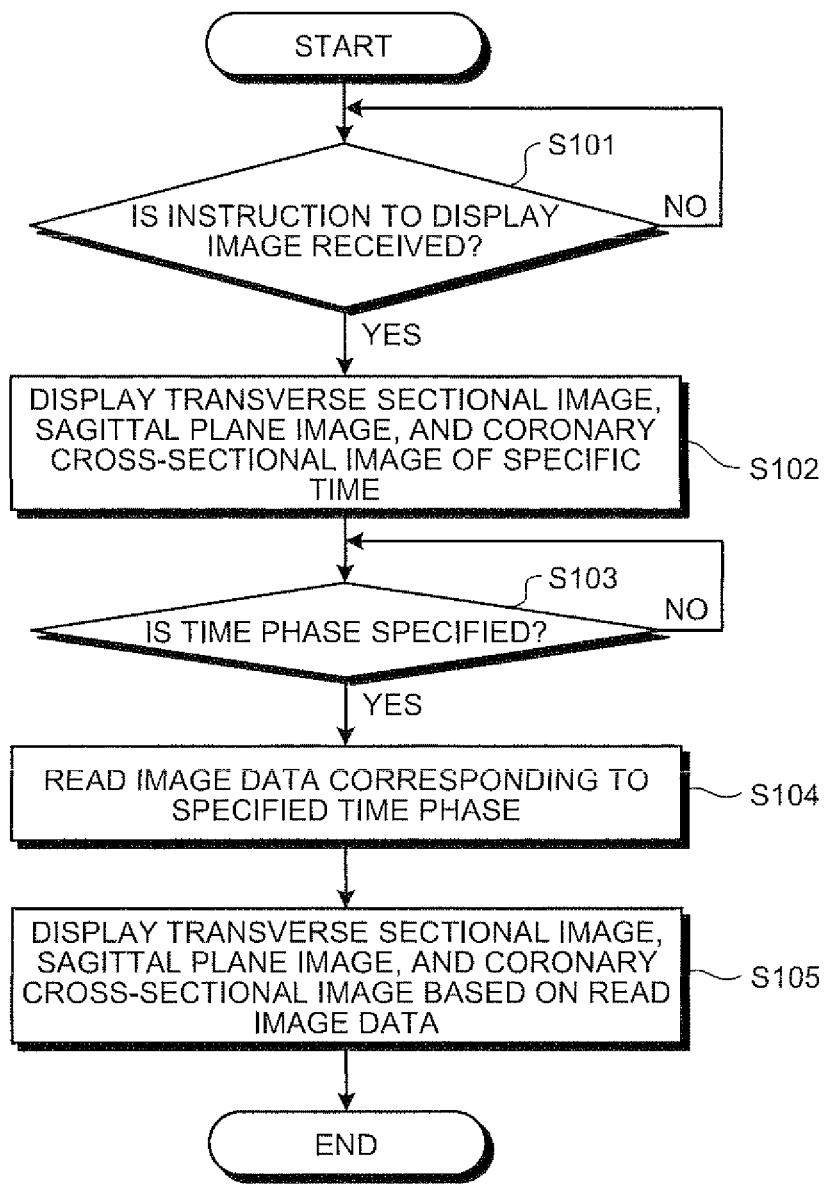
FIG. 3 is a flowchart of a process procedure performed by a control unit in a computing system.

A process procedure performed by the control unit 17 in the computing system 10 explained above is explained below. FIG. 3 is a flowchart of a process procedure performed by the control unit 17 in the computing system 10. A case of using the image viewing screen 100 shown in FIG. 2 is explained below as an example.

As shown in FIG. 3, when the input receiving unit 17a receives an instruction to display an image from an operator via the input unit 16, (Yes at Step S101), the control unit 17 in the computing system 10 displays an axial image, a sagittal image, and a coronal image of a specific time (for example, a time of the first R wave) in the image display area on the image viewing screen 100 displayed on the display unit 15 (Step S102).

Subsequently, when the operator specifies a time phase via the user interface area on the image viewing screen 100 (Yes at Step S103), the screen-display control unit 17b reads image data corresponding to the specified time phase from the storage unit 14 (Step S104), creates an axial image, a sagittal image, and a coronal image based on the read image data, and displays the respective created images in the image display area on the image viewing screen 100 (Step S105).

As described above, according to the first embodiment, the storage unit 14 stores therein image data in a manner associated with multiple dimensions, such as three spatial dimensions and time. The input receiving unit 17a displays images of specific dimensions, such as cardiac cine images of three spatial dimensions, and receives input information about another dimension, such as cardiac time phase. When the input receiving unit 17a receives input information about another dimension, the screen-display control unit 17b then reads image data corresponding to the dimension of the received information from image data stored by the storage unit 14, and displays images of the specific dimensions, such as cine images of three spatial dimensions, based on the read image data, so that the operator can efficiently observe the images by associating them with the multiple dimensions.

Usually when imaging a heart by using an MRI apparatus, a typically used method is reconstructing image data per cardiac time phase from data that is collected across a plurality of heart beats. For example, there is a method of reconstructing an image by dividing k-space into a plurality of regions called segments and collecting data of one segment with respect to each heart beat (also called Segmented Fast Field Echo (FFE)). According to the method, data of one segment includes a plurality of phase encoding data.

In this way, according to the first embodiment, even when displaying an image reconstructed from data collected across heart beats, the control unit 17 displays the reconstructed image together with an electrocardiographic waveform (or a pattern of pulse wave) of one heart beat. Accordingly, the operator can efficiently observe images in phases in one heart beat.

Although the first embodiment is explained in a case where the MRI apparatus 50 displays images in a manner associated with three spatial dimensions and cardiac time phase, the present invention is not limited to this, and can be applied to various dimensions related to time in addition to cardiac time phase. As a second embodiment of the present invention, a case of displaying an image of three spatial dimensions in a manner associated with another dimension related to time is explained below.

An MRI apparatus according to the second embodiment basically includes the same configuration as that of the MRI apparatus 50 shown in FIG. 1, so that detailed explanations of the configuration are omitted. In the following description, mutual relation and a flow of data between units included in the MRI apparatus according to the second embodiment are explained in detail, and an example of an image viewing screen displayed by the control unit 17 (the input receiving unit 17a) is explained.

Figure 4:
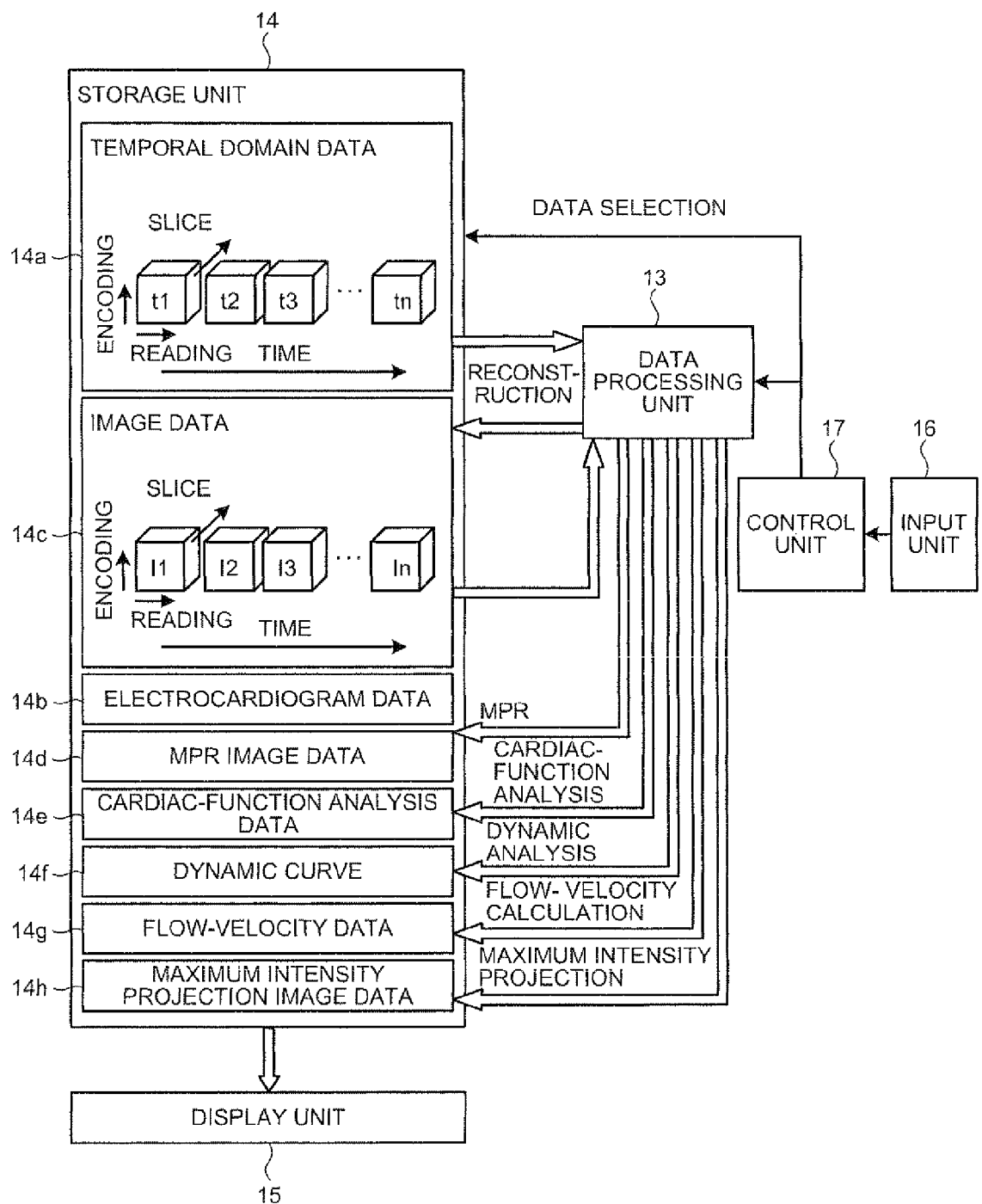
FIG. 4 is a schematic diagram for explaining mutual relation and a flow of data between units included in an MRI apparatus according to a second embodiment of the present invention.

FIG. 4 is a schematic diagram for explaining mutual relation and a flow of data between units included in the MRI apparatus according to the second embodiment. As shown in FIG. 4, the storage unit 14 receives magnetic resonance signal data collected through an imaging pulse sequence and transferred from the data collecting unit 12, and stores therein the transferred data as temporal domain data 14a.

The temporal domain data 14a generally has a three-dimensional structure that includes readout ("reading" shown in FIG. 4), phase encoding ("encoding" shown in FIG. 4), and slice. If data obtained at a different time is present, for example, in a case of ECG-gated imaging or dynamic imaging, the temporal domain data 14a can have a four-dimensional structure that further includes a temporal dimension.

If ECG-gated imaging, peripheral blood-flow synchronized imaging, or breath synchronized imaging is performed, the storage unit 14 stores therein the temporal domain data 14a and biological information about the subject P being scanned as electrocardiogram data 14b.

To a group of data having such time-base information, time information, for example, t1 to tn shown in FIG. 4, is given to each piece of data in the group of data. Moreover, for example, if data including information about chemical shift is collected, the group of data includes a dimension of chemical shift, which is not shown in FIG. 2.

Furthermore, when the data processing unit 13 performs on the group of data a two-dimensional or three-dimensional Fourier transformation in accordance with the dimensions of the data, image data 14c is reconstructed, and then the image data 14c that is reconstructed is stored in another domain of the storage unit 14. Usually, the image data 14c that is reconstructed is three-dimensional data, and if the image data 14c includes time-base information, time information, such as I1 to In shown in FIG. 4, is given to each piece of data in the group of data, so that the image data 14c has a four-dimensional structure.

For example, in a case of using the image viewing screen 100 shown in FIG. 2, when the operator specifies a cardiac time phase, i.e., a time point from an R wave, the control unit 17 selects one piece of the image data 14c given with time information corresponding to the specified time from a group of n pieces of image data that are I1 to In of the image data 14c stored by the storage unit 14. The control unit 17 performs cross-section conversion (MPR) of the selected image data by controlling the data processing unit 13, thereby outputting the obtained MPR image data (a coronal image, an axial image, and a sagittal image) 14d to the display unit 15.

To obtain information needed for diagnosis in addition to information directly displayed as an MPR image on the display unit 15, the data processing unit 13 sometimes performs post-processing on the image data 14c explained above in some cases. Such processing is generally called a cardiac function analysis. For example, when there is image data of three spatial dimensions obtained through ECG-gated imaging, contours of myocardial intima of the left ventricle can be extracted by using the image data, and cardiac-function analysis data 14e, such as sequential variations in the left ventricular volume within one heart beat, can be obtained.

In addition to the above, there are various kinds of data as data output via such cardiac function analysis, for example, myocardial-wall thickness variations cardiac output, ejection fraction rate, and an image called "Bull's eye" that depicts those values in development elevation.

Figure 5:
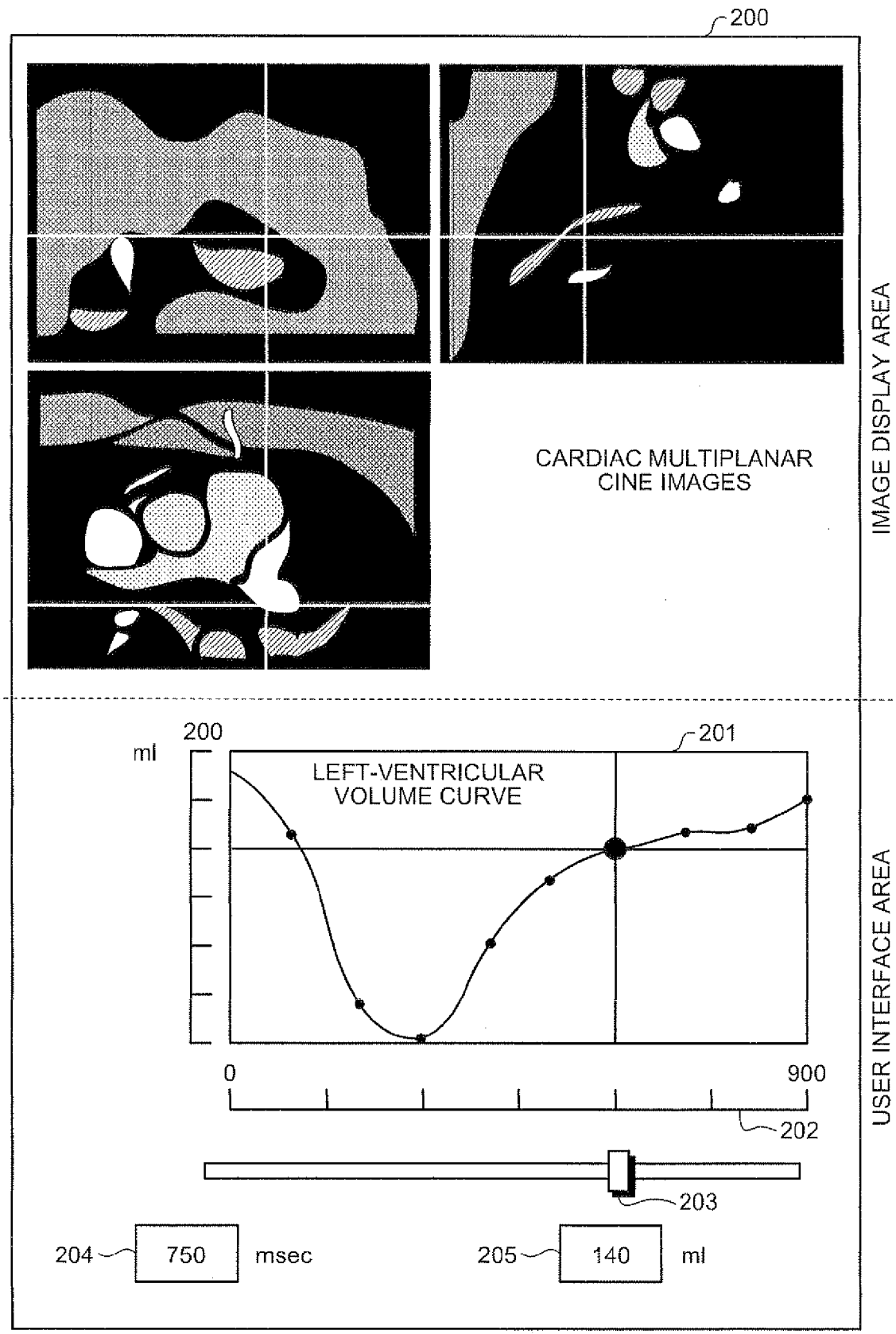
FIG. 5 is a schematic diagram illustrating an example of an image viewing screen when displaying cine Magnetic Resonance (MR) images and a left-ventricular volume curve according to the second embodiment.

A case of displaying an image of three spatial dimensions in a manner associated with, for example, a left-ventricular volume curve obtained via such cardiac function analysis is explained below. FIG. 5 is a schematic diagram that depicts an example of an image viewing screen when displaying cine MR images and a left-ventricular volume curve.

As shown in FIG. 5, in this case, an image viewing screen 200 includes, for example, an image display area for displaying images of three spatial dimensions, and a user interface area for receiving input information about a cardiac time phase of the left-ventricular volume curve.

In the image display area, for example, cardiac cine MRI images are displayed similarly to the image viewing screen 100 shown in FIG. 2 (the cardiac multiplanar cine images shown in FIG. 5).

On the other hand, in the user interface area, for example, as shown with a left-ventricular volume curve 201 in FIG. 5, the left ventricular volume calculated in the post-processing are displayed in a graph of values plotted at respective time points in one cardiac cycle. Furthermore, a scale 202 that indicates cardiac time phases, and a slider 203 and an input box 204 for specifying a phase are displayed in the user interface area.

According to the method, the operator can observe a form of the heart in accordance with a state of the ventricular volume. Furthermore, as an input box 205 for specifying a left ventricular volume (ml) corresponding to the vertical axis of the graph is displayed, the operator can select a phase representing a left ventricular volume of interest, and can observe a form of the heart in the phase as an image.

The operator specifies a time point that the operator intends to display by using an input device of the input unit 16, such as a mouse or a keyboard. The control unit 17 selects one piece of image data given with corresponding time information from the group of n pieces of image data that are I1 to In of the image data 14c based on information about the time point obtained by the input unit 16, and outputs to the display unit 15 an MPR image on which the data processing unit 13 has performed cross-section conversion. If the operator desires to display an image at a time representing a specific left ventricular volume, the operator can select a desired image by displaying a value of the left ventricular volume corresponding to the vertical axis of the graph in a numerical value.

As an example of post-processing when there is data of another time sequence, there are a so-called dynamic curve and a flow-velocity curve. The dynamic curve is a plot of pixel values in a region of interest specified by the operator on the screen plotted in the temporal axis direction. The flow-velocity curve is a plot of flow velocities of spin in a region of interest obtained from data obtained by a phase contrast method and plotted in the temporal axis direction. Such information is similarly stored in the storage unit 14 as a dynamic curve 14f and flow-velocity data 14g. Moreover, when the data processing unit 13 performs Maximum Intensity Projection (MIP) on image data, MIP image data 14h is stored in the storage unit 14.

Figure 6:
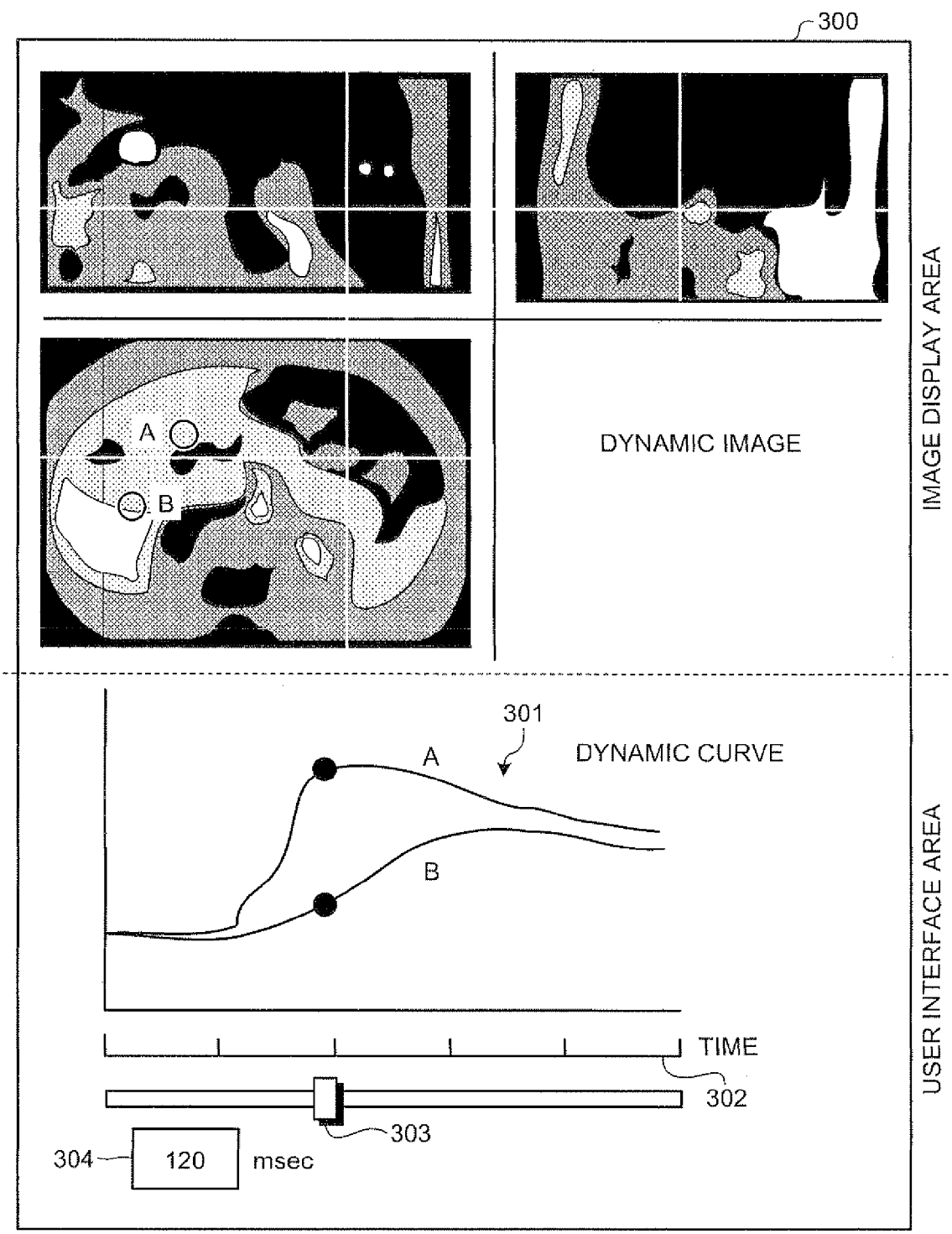
FIG. 6 is a schematic diagram illustrating an example of an image viewing screen when displaying dynamic MR images and dynamic curves according to the second embodiment.
Figure 7:
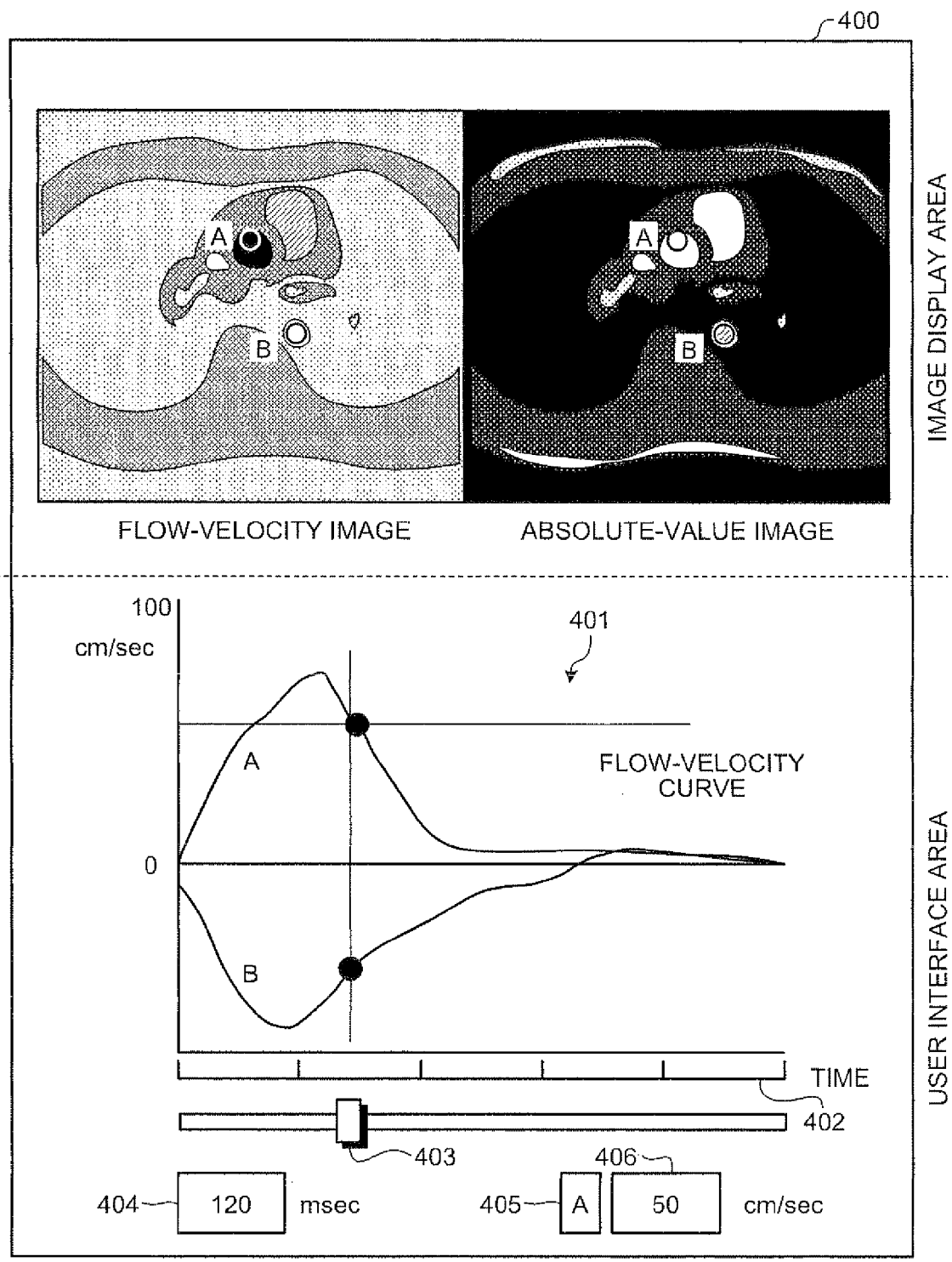
FIG. 7 is a schematic diagram illustrating an example of an image viewing screen when displaying a flow-velocity image and flow-velocity curves according to the second embodiment.

A case of displaying an image of three spatial dimensions in a manner associated with, for example, a dynamic curve or a flow-velocity curve obtained by such post-processing is explained below. FIG. 6 is a schematic diagram that depicts an example of an image viewing screen when displaying dynamic MR images and dynamic curves, and FIG. 7 is a schematic diagram that depicts an example of an image viewing screen when displaying a flow-velocity image and flow-velocity curves.

At first, a case of displaying an image of three spatial dimensions in a manner associated with a dynamic curve is explained below. As shown in FIG. 6, in this case, an image viewing screen 300 includes, for example, an image display area for displaying images of three spatial dimensions, and a user interface area for receiving input information about dynamic curve.

In the image display area, for example, images of three dimensions of dynamic MR obtained by continuous imaging that follows sequential variations after infusion of a contrast agent (the dynamic images shown in FIG. 6) are displayed. FIG. 6 depicts a case where images of three dimensions of an abdomen are displayed. Moreover, Regions Of Interest (ROI) in circles (circles A and B shown in FIG. 6) are displayed on the images.

On the other hand, in the user interface area, for example, a graph (dynamic curves) 301 that depicts, in time sequence, signal values of the regions indicated by the ROIs set on the image display area is displayed. Furthermore, a scale 302 that indicates time, a slider 303 and an input box 304 for specifying a time are displayed in the user interface area.

The operator can display an image corresponding to a time of interest or a signal value of an ROI by using the interface, thereby being able to observe an image contrast at the time. Moreover, the operator can set an ROI on an image in a phase in which a lesion is easily observed by observing images while moving the slider 303, thereby being able to see a dynamic curve of the portion.

Although an example of observing sequential change in an effect of contrast enhancement is explained above, in addition, the operator can perform observation of a functional image created by functional MRI (fMRI) by using an effect of Blood Oxygenation Level Dependent (BOLD), or image observation when there is data created by sequentially scanning the same portion for therapeutic effect determination and follow-up of the same patient.

Then, a case of displaying an image of three spatial dimensions in a manner associated with a flow-velocity curve is explained below. As shown in FIG. 7, in this case, an image viewing screen 400 includes, for example, an image display area for displaying images of three spatial dimensions, and a user interface area for receiving input information about flow-velocity curve.

In the image display area, for example, a flow-velocity image and an absolute-value image of a large cardiovascular system obtained by Phase Contrast Magnetic Resonance Angiography (PCMRA) is displayed. According to an example shown in FIG. 7, the left image is a flow-velocity image, and the right image is an absolute-value image. Moreover, ROIs are displayed in circles (circles A and B shown in FIG. 7) on the images. Generally, a pixel value of each pixel on the flow-velocity image reflects a flow velocity at the position of the pixel.

On the other hand, in the user interface area, for example, flow-velocity curves 401 that depict blood flow velocities of aorta ascendens and descendens in the regions indicated with the ROIs set on the images in the image display area in an associated manner with a phase in a cardiac cycle is displayed. Furthermore, a scale 402 that indicates time, a slider 403 and an input box 404 for specifying a time, an input box 405 for specifying an ROI, and an input box 406 for specifying a flow velocity are displayed in the user interface area.

The operator can display an image corresponding to a time of interest or a flow velocity of an ROI similarly to the image viewing screen 300 shown in FIG. 6, thereby being able to observe an image contrast and a form at the time with the flow-velocity image and the absolute-value image, respectively. Moreover, the operator can set an ROI on an image in a phase in which a blood vessel is easily observed by observing images while moving the slider 403, thereby being able to display a flow-velocity curve of the portion. According to the example, the images are two-dimensional images because of a data collection method, so that only axial images are displayed.

As described above, according to the second embodiment, the storage unit 14 stores therein image data in a manner associated with three spatial dimensions and time. The input receiving unit 17a displays images of three spatial dimensions, and receives input information about a cardiac time phase. When the input receiving unit 17a receives input information about a cardiac time phase, the screen-display control unit 17b then reads image data corresponding to the cardiac time phase from image data stored by the storage unit 14, and displays images of three spatial dimensions based on the read image data, so that the operator can efficiently observe the images by associating them with three spatial dimensions and cardiac time phase.

Although the above embodiments are explained in cases of displaying images of three spatial dimensions in a manner associated with a dimension related to time, dimensions of an image taken by the MRI apparatus are not only a dimension related to time, but can be a dimension related to chemical shift. As a third embodiment of the present invention, a case of displaying an image in a manner associated with chemical shift is explained below.

An MRI apparatus according to the third embodiment also basically includes the same configuration as that of the MRI apparatus 50 shown in FIG. 1, so that detailed explanations of the configuration are omitted. In the following description, mutual relation and a flow of data between units included in the MRI apparatus according to the third embodiment are explained, and an example of an image viewing screen displayed by the control unit 17 (the input receiving unit 17a) is explained.

Figure 8:
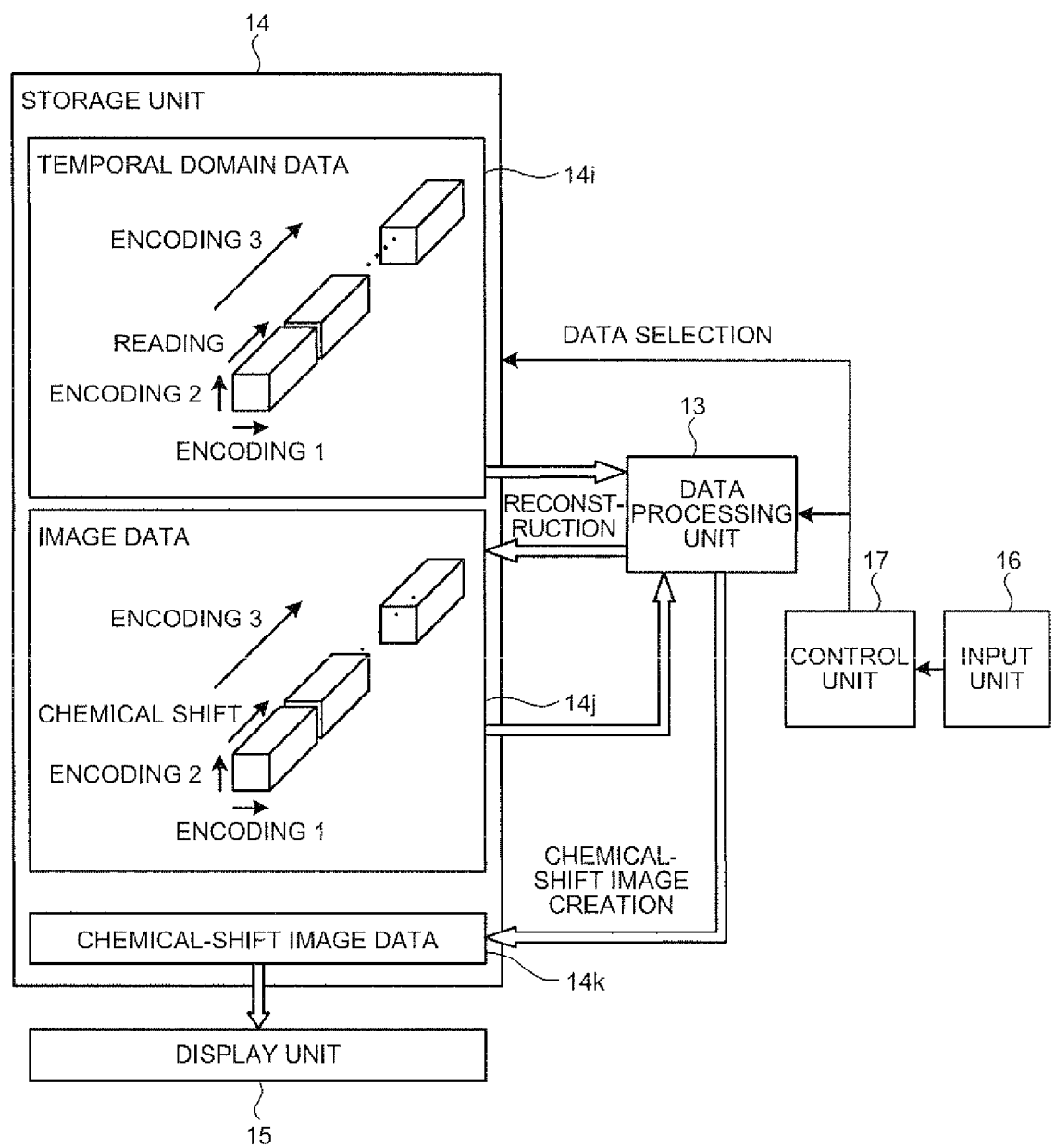
FIG. 8 is a schematic diagram for explaining mutual relation and a flow of data between units included in an MRI apparatus according to a third embodiment of the present invention.

Specifically, according to the third embodiment, it is assumed that imaging is performed in accordance with Magnetic Resonance Spectroscopic Imaging (MRSI) that phase encoding is performed in three spatial dimensional directions, and magnetic resonance signals are collected without readout gradient. FIG. 8 is a schematic diagram for explaining mutual relation and a flow of data between units included in an MRI apparatus according to the third embodiment.

As shown in FIG. 8, temporal domain data 14i obtained by the method is four-dimensional data that one dimension of frequency is added to three spatial dimensions, and as a four-dimensional Fourier transformation is performed on the temporal domain data 14i, image data 14j added with spectrum information is obtained.

Figure 9:
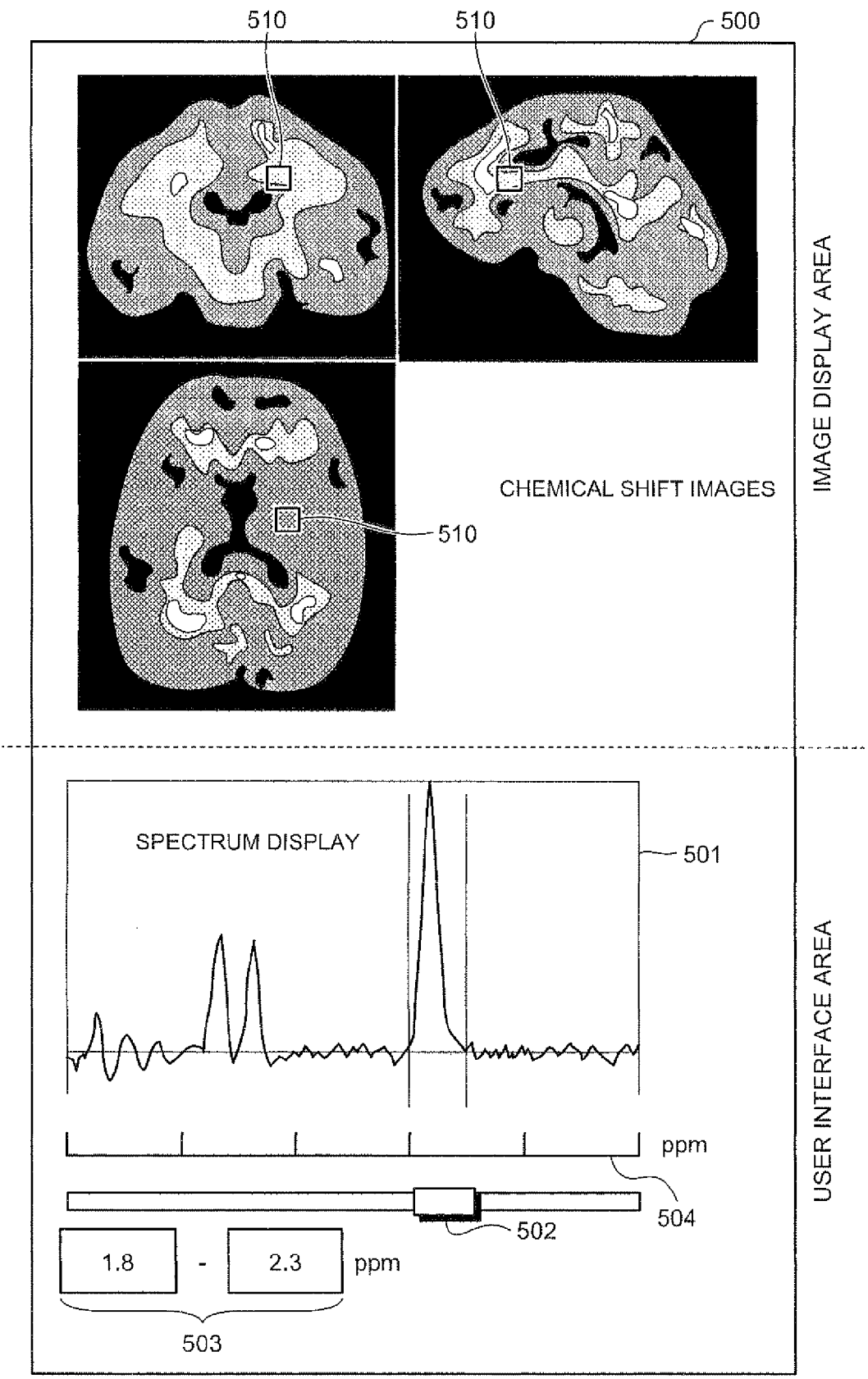
FIG. 9 is a schematic diagram illustrating an example of an image viewing screen when displaying chemical shift images and spectrum information according to the third embodiment.

A case of displaying an image of three dimensions in a manner associated with, for example, spectrum information obtained by MRSI is explained below. FIG. 9 is a schematic diagram that depicts an example of an image viewing screen when displaying chemical shift images and spectrum information.

As shown in FIG. 9, in this case, an image viewing screen 500 includes, for example, an image display area for displaying images of three spatial dimensions, and a user interface area for receiving input information about spectrum information.

In the image display area, for example, chemical shift images of spatial three dimensions obtained by MRSI are displayed. Additionally, ROIs 510 in rectangles are displayed on the images.

On the other hand, in the user interface area, for example, a proton spectrum 501 in the regions indicated by the ROIs 510 set on the images in the image display area is displayed. The horizontal axis shown in FIG. 9 denotes chemical shift, which is an amount of deviation to a normal reference material. The amount of deviation is shown in ppm as unit. Furthermore, a scale 504 that indicates the amount of deviation of chemical shift, and a slider 502 and an input box 503 for specifying a range of chemical shift are displayed in the user interface area. The two lines shown on the proton spectrum 501 are synchronized with the range of chemical shift specified by the operator.

The operator can specify a range of chemical shift of interest via the input unit 16, and can display an image that depicts a distribution of substances around the frequency band (Chemical Shift Image (CSI)).

To observe a spatial distribution of components that has a specific chemical shift among the data displayed in FIG. 8, the operator then selects a range of chemical shift of interest by operating the slider 502 or inputting a numerical value into the input box 503 by using an input device, such as a mouse or a keyboard, of the input unit 16. When the operator selects the range, the control unit 17 selects only image data specified from among the image data 14j based on the information about the chemical shift input by the operator, and then displays the selected image data to the display unit 15.

Figure 10:
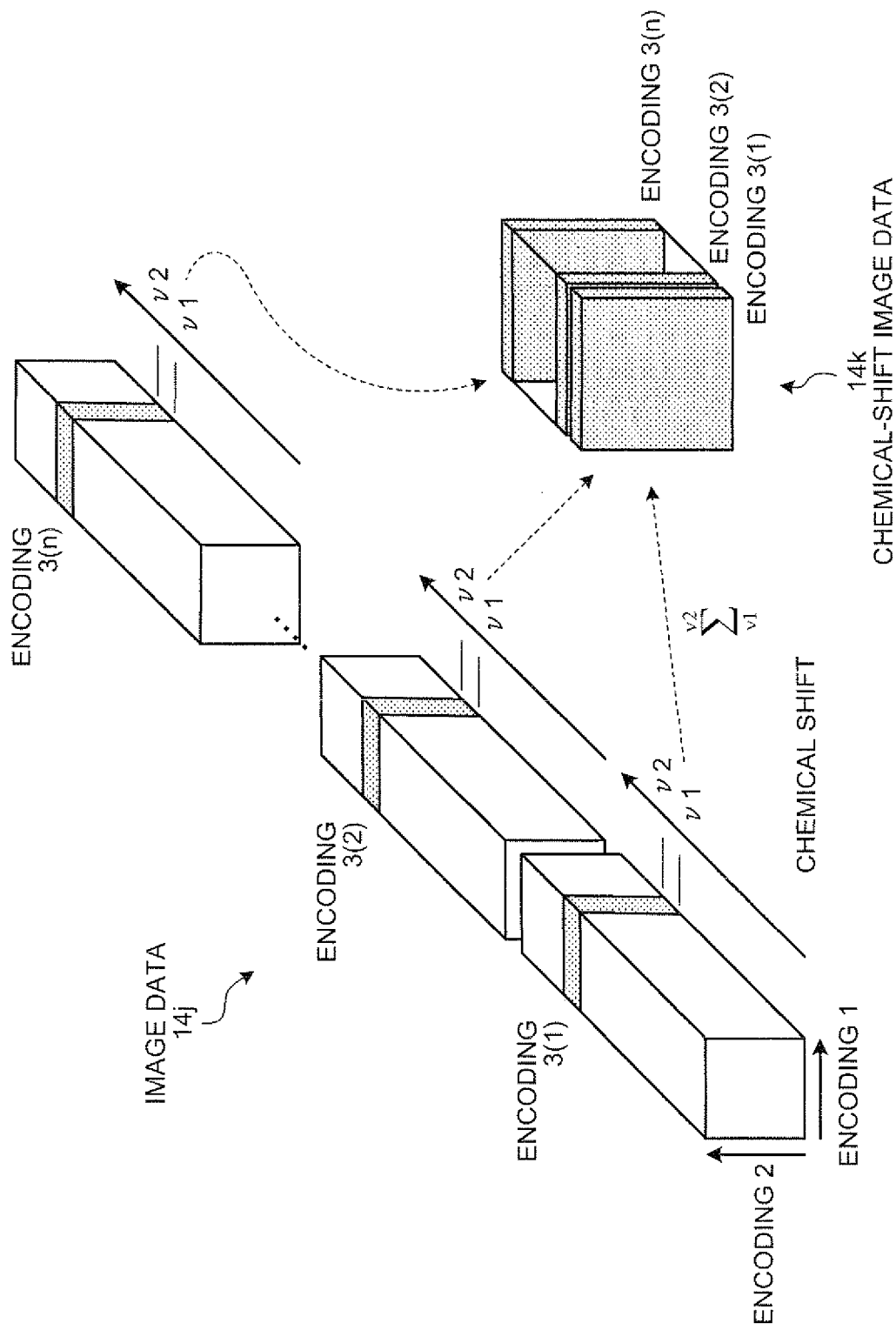
FIG. 10 is a schematic diagram for explaining selection of image data based on information about chemical shift according to the third embodiment.

The process described above is explained below in more detail. FIG. 10 is a schematic diagram for explaining selection of image data based on information about chemical shift. For example, suppose a range of chemical shift input by the operator is from v1 to v2. In such case, as shown in FIG. 10, the control unit 17 adds pixel values of v1 to v2 in the same spatial coordinates among the image data 14j, and creates chemical-shift image data 14k of three dimensions. The control unit 17 then outputs the chemical-shift image data 14k that is created to the display unit 15.

As described above, according to the third embodiment, the storage unit 14 stores therein image data in a manner associated with three spatial dimensions and chemical shift. The input receiving unit 17a displays images of three spatial dimensions, and receives input information about chemical shift. When the input receiving unit 17a receives input information about chemical shift, the screen-display control unit 17b then reads image data corresponding to the chemical shift from image data stored by the storage unit 14, and displays images of three spatial dimensions based on the read image data, so that the operator can efficiently observe the images by associating them with three spatial dimensions and chemical shift.

Although the above embodiments are explained in cases of displaying image data in a manner associated with four dimensions where one dimension of time or chemical shift is added to three spatial dimensions, there is another case where image data has more dimensions depending on kinds of imaging. For example, to collect chemical shift images of three spatial dimensions in time sequence, data has five dimensions that time and chemical shift are added to three spatial dimensions. As a fourth embodiment of the present invention, a case of displaying two or more dimensions other than spatial dimensions is explained below.

An MRI apparatus according to the fourth embodiment also basically includes the same configuration as that of the MRI apparatus 50 shown in FIG. 1, so that detailed explanations of a configuration are omitted. In the following description, mutual relation and a flow of data between units included in the MRI apparatus according to the fourth embodiment are explained, and an example of an image viewing screen displayed by the control unit 17 (the input receiving unit 17a) is explained.

Figure 11:
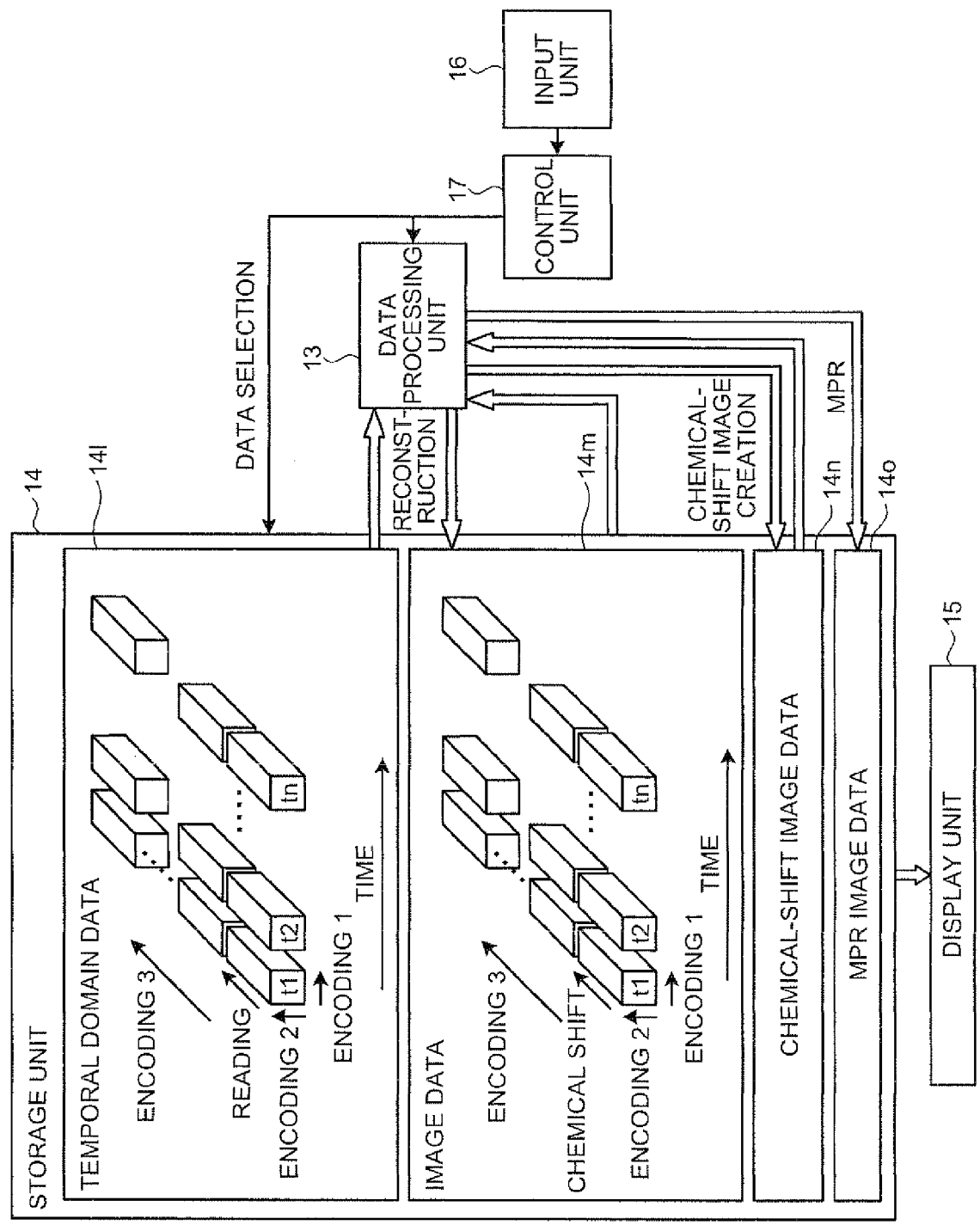
FIG. 11 is a schematic diagram for explaining mutual relation and a flow of data between units included in an MRI apparatus according to a fourth embodiment of the present invention.

Specifically, according to the fourth embodiment, it is assumed that MRSI shown in FIG. 8 is performed repeatedly a plurality of number of times. FIG. 11 is a schematic diagram for explaining mutual relation and a flow of data between units included in the MRI apparatus according to the fourth embodiment.

As shown in FIG. 11, in this case, temporal domain data 14*l* stored by the storage unit 14 has five dimensions as further added with a dimension of time. As the data processing unit 13 performs a four-dimensional Fourier transformation on the temporal domain data 14*l*, MRSI image data 14*m* in time sequence is obtained.

Moreover, a plurality of chemical-shift image data 14*n* is obtained with respect to data of respective times of the MRSI image data 14*m* according to the method explained with reference to FIG. 10. Furthermore, MPR image data 14*o* is obtained as the data processing unit 13 performs cross-section conversion (MPR) on the MRSI image data 14*m*.

Figure 12:
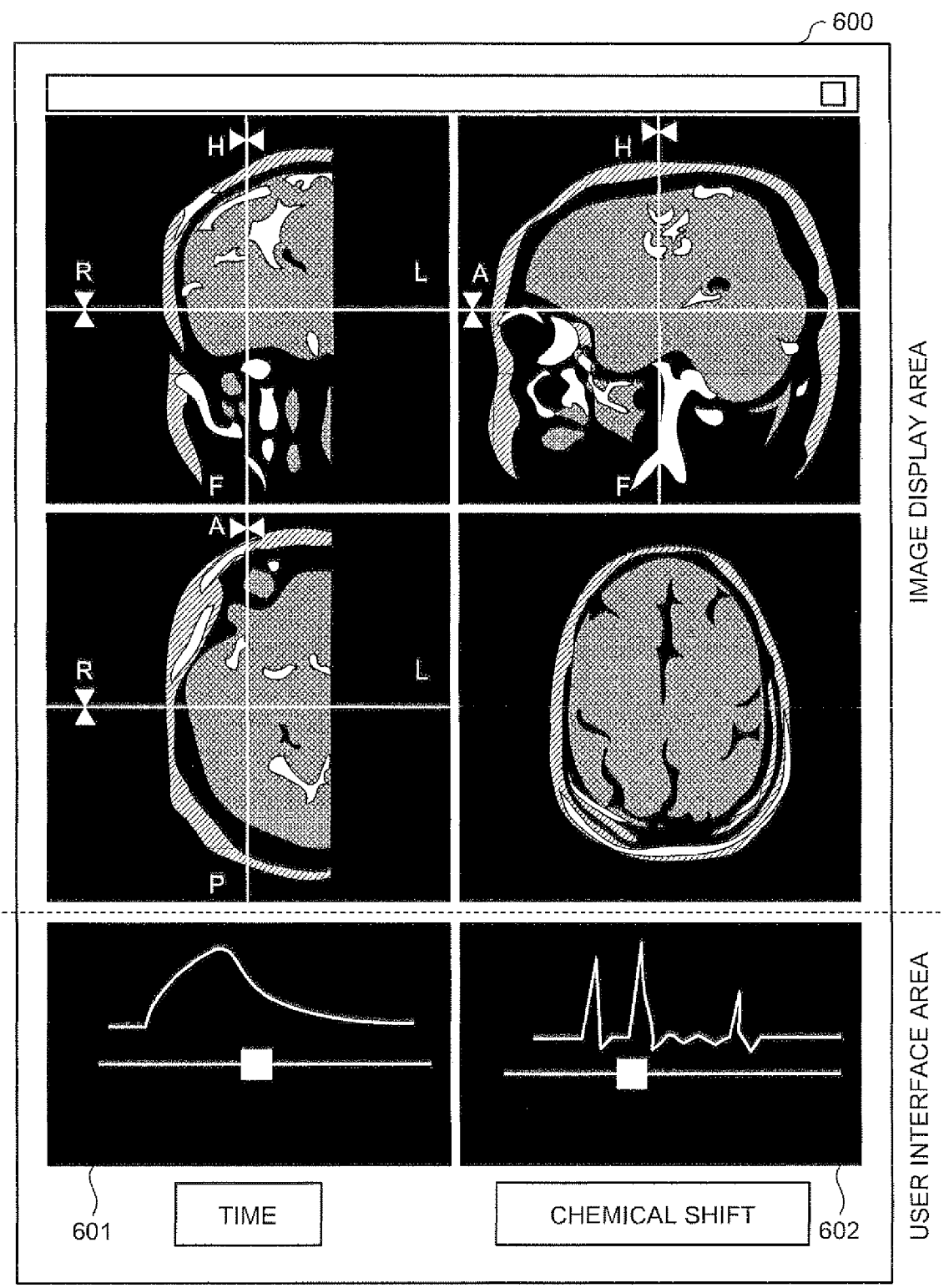
FIG. 12 is a schematic diagram illustrating an example of an image viewing screen when displaying two or more dimensions other than spatial dimensions according to the fourth embodiment.

A case of outputting spectrum information obtained by the repeated MRSI onto an image viewing screen is explained below. FIG. 12 is a schematic diagram that depicts an example of an image viewing screen when displaying two or more dimensions other than spatial dimensions.

As shown in FIG. 12, in this case, an image viewing screen 600 includes, for example, an image display area for displaying images of three spatial dimensions, and a user interface area for receiving input information about spectrum information.

In the image display area, for example, cine MR images are displayed similarly to the image viewing screen 100 shown in FIG. 2.

On the other hand, in the user interface area, a slider 601 for setting a time, and a slider 602 for setting chemical shift are displayed. Accordingly, data of multiple dimensions can be displayed in a manner associated with respective dimensions.

The operator specifies a time that the operator desire to observe, via the input unit 16. When the operator specifies the time, the control unit 17 selects image data of the specified time from among the chemical-shift image data 14*n*, and then outputs the selected image data to the display unit 15.

As described above, according to the fourth embodiment, the storage unit 14 stores therein image data in a manner associated with three spatial dimensions and other two or more dimensions. The input receiving unit 17a displays images of three spatial dimensions, and receives input information about two or more other dimensions. When the input receiving unit 17a receives input information about two or more other dimensions, the screen-display control unit 17b then reads image data corresponding the dimensions of the received information from image data stored by the storage unit 14, and displays images of three spatial dimensions based on the read image data, so that the operator can efficiently observe the images by associating them with three spatial dimensions and two or more other dimensions.

Although the above embodiments are explained in cases where conceptions of time and chemical shift in addition to space are introduced in image data; among cases of imaging with an MRI apparatus, there is another case where the same portion is scanned a plurality of times by changing scanning parameters that have an influence on a image contrast, for example, Echo Time (TE), Inversion Time (TI), flip angle, flip angle and frequency of fat-suppression pulse, and b value of diffusion emphasized imaging (value that indicates the strength of a Motion Probing Gradient (MPG) pulse used in a diffusion emphasized imaging). In such case, the operator needs to observe change in the contrast of an image by changing scanning parameters in succession. A case of performing a scan by changing scanning parameters is explained below as a fifth embodiment of the present invention.

An MRI apparatus according to the fifth embodiment also basically includes the same configuration as that of the MRI apparatus 50 shown in FIG. 1, so that detailed explanations of a configuration are omitted. In the following description, mutual relation and a flow of data between units included in the MRI apparatus according to the fifth embodiment are explained, and an example of an image viewing screen displayed by the control unit 17 (the input receiving unit 17a) is explained.

Figure 13:
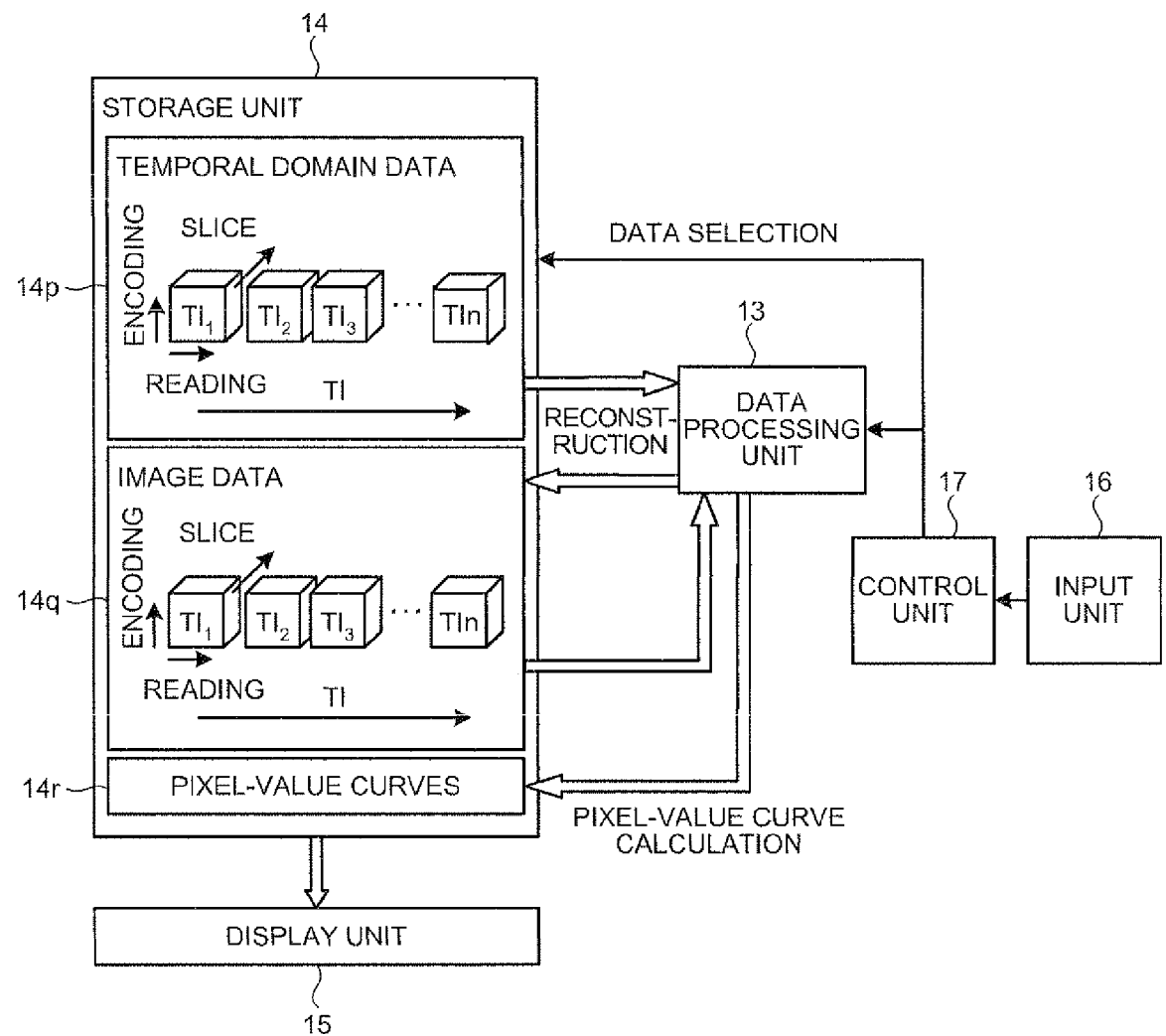
FIG. 13 is a schematic diagram for explaining mutual relation and a flow of data between units included in an MRI apparatus according to a fifth embodiment of the present invention.

FIG. 13 is a schematic diagram for explaining mutual relation and a flow of data between units included in the MRI apparatus according to the fifth embodiment. As shown in FIG. 13, temporal domain data 14*p* stored by the storage unit 14 includes a group of a plurality of data of imaging taken with different scanning parameters, for example, different inversion times TI ($TI_1$, $TI_2$, $TI_3$, . . . , $TI_n$) in imaging according to inversion recovery. Furthermore, image data 14*q* of a plurality of TIs ($TI_1$, $TI_2$, $TI_3$, . . . , $TI_n$) obtained by reconstructing the temporal domain data 14*p* are stored in the storage unit 14. The inversion time TI is a period from application of an inversion pulse to the start of a scan.

Figure 14:
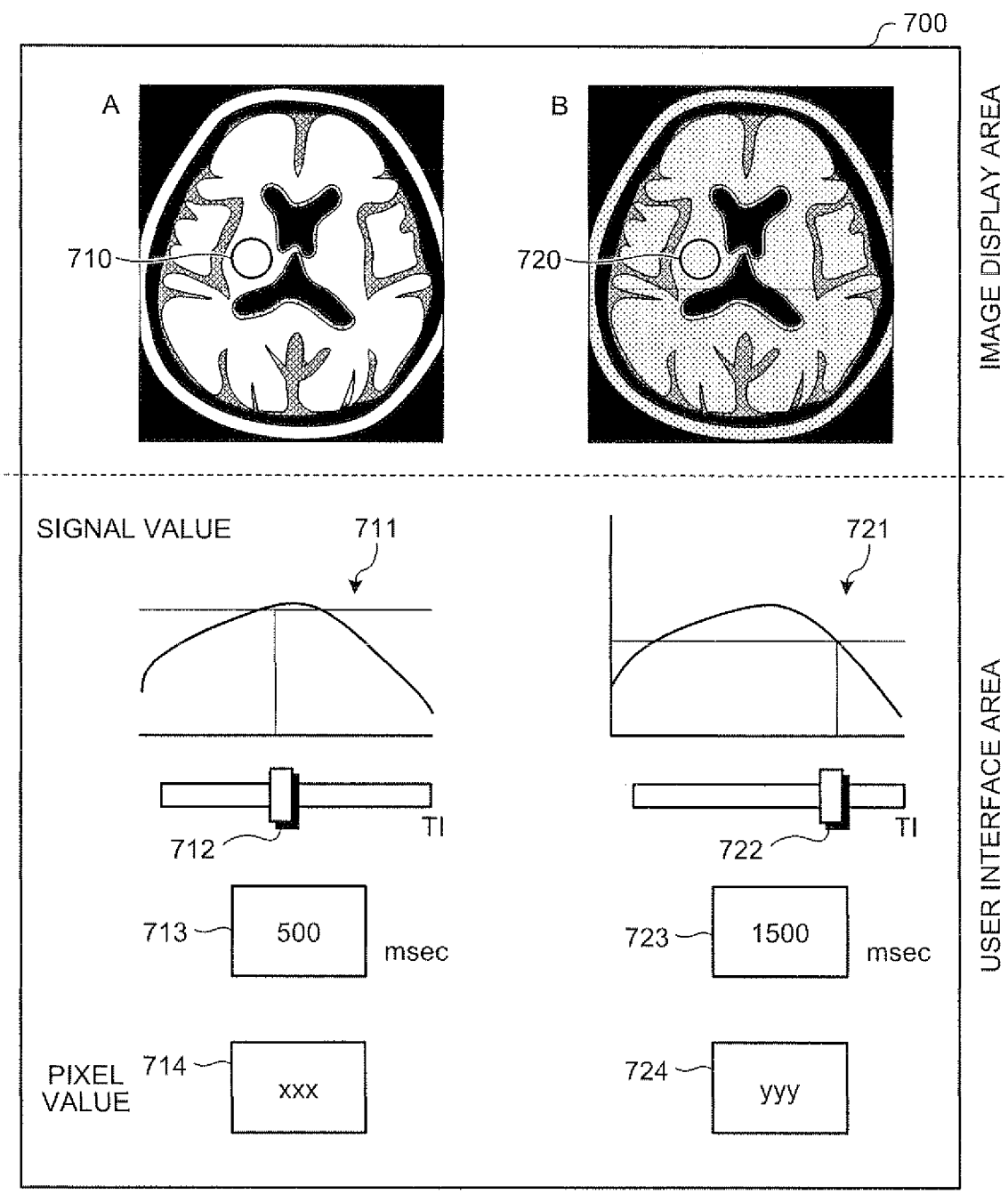
FIG. 14 is a schematic diagram illustrating an example of an image viewing screen when displaying a plurality of images taken with different scanning parameters according to the fifth embodiment.

The following description is explained in a case of displaying images individually taken in accordance with respective parameter settings into two or more frames, for example, to compare images taken in accordance with two or more different scanning parameters. FIG. 14 is a schematic diagram that depicts an example of an image viewing screen when displaying a plurality of images in accordance with different scanning parameters.

As shown in FIG. 14, in this case, an image viewing screen 700 includes, for example, an image display area for displaying two images, and a user interface area for receiving input information about scanning parameter information.

In the image display area, for example, two images taken in accordance with different scanning parameters (A and B shown in FIG. 14) are displayed. ROIs 710 and 720 in circles are displayed on the images.

On the other hand, in the user interface area, for example, pixel-value curves 711 and 721 created by plotting with respect to TI average signal values in the regions shown as ROIs 710 and 720 set on the images in the image display area, respectively. Furthermore, in the user interface area, sliders 712 and 722 and input boxes 713 and 723 for specifying a time of TI, and display boxes 714 and 724 for displaying average signal values in the ROIs 710 and 720, respectively, are displayed for the respective images. The two images shown in FIG. 14 depict images taken using two points of TIs specified with the sliders 712 and 722, respectively, among images of the same cross-section taken at a plurality of TIs.

Specifically, the operator specifies TI with respect to each of the images by operating the slider 712 or 722 or inputting numerical values into the input box 713 or 723 shown in FIG. 14. When the operator specifies TIs, the control unit 17 selects images of the specified TIs from among a group of image data of the image data 14*q*, and outputs the selected images to the display unit 15.

Moreover, the operator sets the ROIs 710 and 720 on the displayed images. When the operator sets the ROIs, the control unit 17 calculates respective average values of pixel values in the ROIs 710 and 720 that is set, stores pixel-value curves 14*r* created by plotting the calculated average values with respect to TI into the storage unit 14 (see FIG. 13), and displays the pixel-value curves 14r together with the respective average pixel-value in the ROIs 710 and 720 of the images of TIs specified with the slider 712 or 722 on the display unit 15 (the pixel-value curves 711 and 721 shown in FIG. 14).

Furthermore, if the operator changes the position of the ROI 710 or 720, the control unit 17 calculates an average pixel-value in the ROI 710 or 720 that is changed, and renews the pixel-value curves 14r stored in the storage unit 14 and the pixel-value curve 711 or 721 displayed in the user interface area.

Accordingly, the operator can easily compare contrasts of two images, for example, by changing TI of one of the images while fixing TI of the other of the images.

Although signal values of one ROI are plotted in this case, the operator can specify, for example, two or more ROIs on the images, and can display plots of a Contrast to Noise ratio (CN ratio) or a Signal to Noise ratio (SN ratio) by calculating differentials or ratios of signal values of the ROIs. Moreover, as a similar display method, instead of parameters for scanning an image, a coefficient of post-processing performed after data collection, for example, image filtering.

As described above, according to the fifth embodiment, the storage unit 14 stores therein image data in a manner associated with parameter values of scanning parameters set for a scan. The input receiving unit 17a displays images of specific dimensions on the display unit 15, and receives input of parameter values of the scanning parameters. When the input receiving unit 17a receives input of parameter values of the scanning parameters, the screen-display control unit 17b then reads image data corresponding the parameter values from image data stored by the storage unit 14, and displays images of the specific dimensions based on the read image data, so that the operator can efficiently observe the images by associating them with the specific dimensions and the scanning parameters.

Although according to the fifth embodiment, a case of displaying images in accordance with inversion times is explained above, the present invention is not limited to this. For example, when displaying an image obtained by ECG-gated imaging or pulse-wave synchronized imaging, the image can be displayed in accordance with a delay time that indicates a period from occurrence of a trigger waveform to be a trigger of a scan (for example, an R wave) to the start of the scan.

Recently, various methods of imaging a blood vessel without using a contrast agent (angiography without contrast agent) have been developed. For example, there is a method of imaging blood-flow dynamic states in a scan area (also called Time-Spatial Labeling Inversion Pulse (Time-SLIP)) by labeling a certain region in a scan area by applying an inversion pulse to the region, and then detecting a blood flow inflowing into or outflowing from the labeled region. When displaying an image taken by such method, the image can be displayed in accordance with, for example, an inversion time that indicates a period from application of an inversion pulse to the start of a scan (also called as TI of the black blood method (BBTI)).

Figure 15:
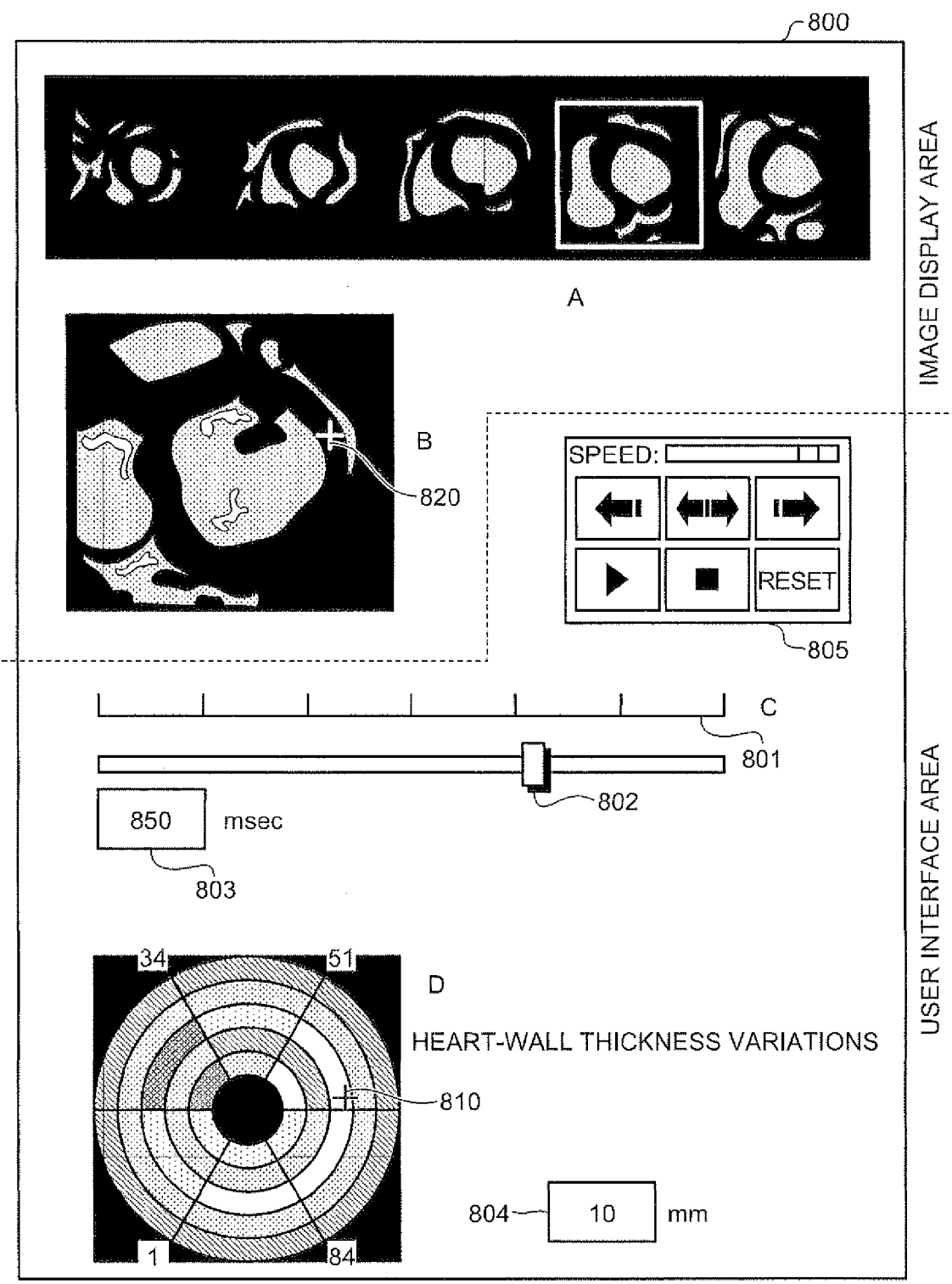
FIG. 15 is a schematic diagram illustrating an example of an image viewing screen when displaying information about a cardiac time phase and a heart wall thickness in relation to cine MR images of a heart according to a sixth embodiment of the present invention.

According to the image viewing screens shown in FIGS. 5, 6, and 7 in the first embodiment, parameters other than space are curves calculated from image data; and a result calculated from image data can include two or more dimensions of information in some cases. As an example of such case, a case of displaying information about cardiac time phase and heart wall thickness in relation to a cine MR image of a heart is explained below as a sixth embodiment of the present invention. FIG. 15 is a schematic diagram that depicts an example of an image viewing screen when displaying information about a cardiac time phase and a heart wall thickness in relation to cine MR images of a heart.

As shown in FIG. 15, in this case, an image viewing screen 800 includes, for example, an image display area for displaying cine MR images, and a user interface area for receiving input information about temporal information and cardiac function information.

In the image display area, for example, images of a certain cardiac time phase among short-axis images of different cross-sections of the left ventricle obtained from cine MR are displayed (A shown in FIG. 15). Moreover, an image of one slice among cardiac cine MR images is displayed in an enlarged view in the image display area (B shown in FIG. 15).

On the other hand, in the user interface area, for example, a development elevation called "Bull's eye" that depicts heart-wall thickness variations created by performing post-processing on the slices of the cardiac cine MR images is displayed in the image display area is displayed (D shown in FIG. 15). Concentrically from the center to the outer side, the development elevation corresponds to slices from the cardiac apex to the cardiac stem.

On the image viewing screen 800, when the operator sets an ROT 810 on the development elevation (a black cross shown on D in FIG. 15), the control unit 17 specifies a slice image corresponding to the position of the ROT 810 from among the cine images displayed in the image display area, and clearly indicates the specified slice image, for example, by highlighting it.

At the same time, the control unit 17 displays an enlarged view of the specified slice image in the image display area (B shown in FIG. 15). Furthermore, the control unit 17 specifies on the displayed enlarged view a position corresponding to the ROI 810 set on the development elevation, and displays an ROI 820 at the specified position (a white cross shown on B in FIG. 15).

The enlarged view displayed in the image display area is a cross-section of the cine images, therefore the enlarged view has a dimension of the time direction Accordingly, similarly to the image viewing screen 100 shown in FIG. 2, as a slider 802 and an input box 803 for specifying a cardiac time phase, an input box 804 for specifying a heart wall thickness, and a continuous display panel 805 for operating continuous display of images are displayed on the user interface area, image selection or animation display can be carried out in accordance with a cardiac time phase.

Accordingly, the operator can easily specify a region of interest on the post-processed development elevation, and can confirm which position in an actual organ the position of the region of interest corresponds to on an original image.

As described above, according to the sixth embodiment, the storage unit 14 stores therein image data in a manner associated with three spatial dimensions, cardiac time phase, and heart wall thickness. The input receiving unit 17a displays images of three spatial dimensions, and receives input information about cardiac time phase and heart wall thickness. When the input receiving unit 17a receives input information about cardiac time phase and heart wall thickness, the screen-display control unit 17b then reads image data corresponding to the dimensions of the received information from image data stored by the storage unit 14, and displays images of three spatial dimensions based on the read image data, so that the operator can efficiently observe the images by associating them with three spatial dimensions, cardiac time phase, and heart wall thickness.

Figure 16:
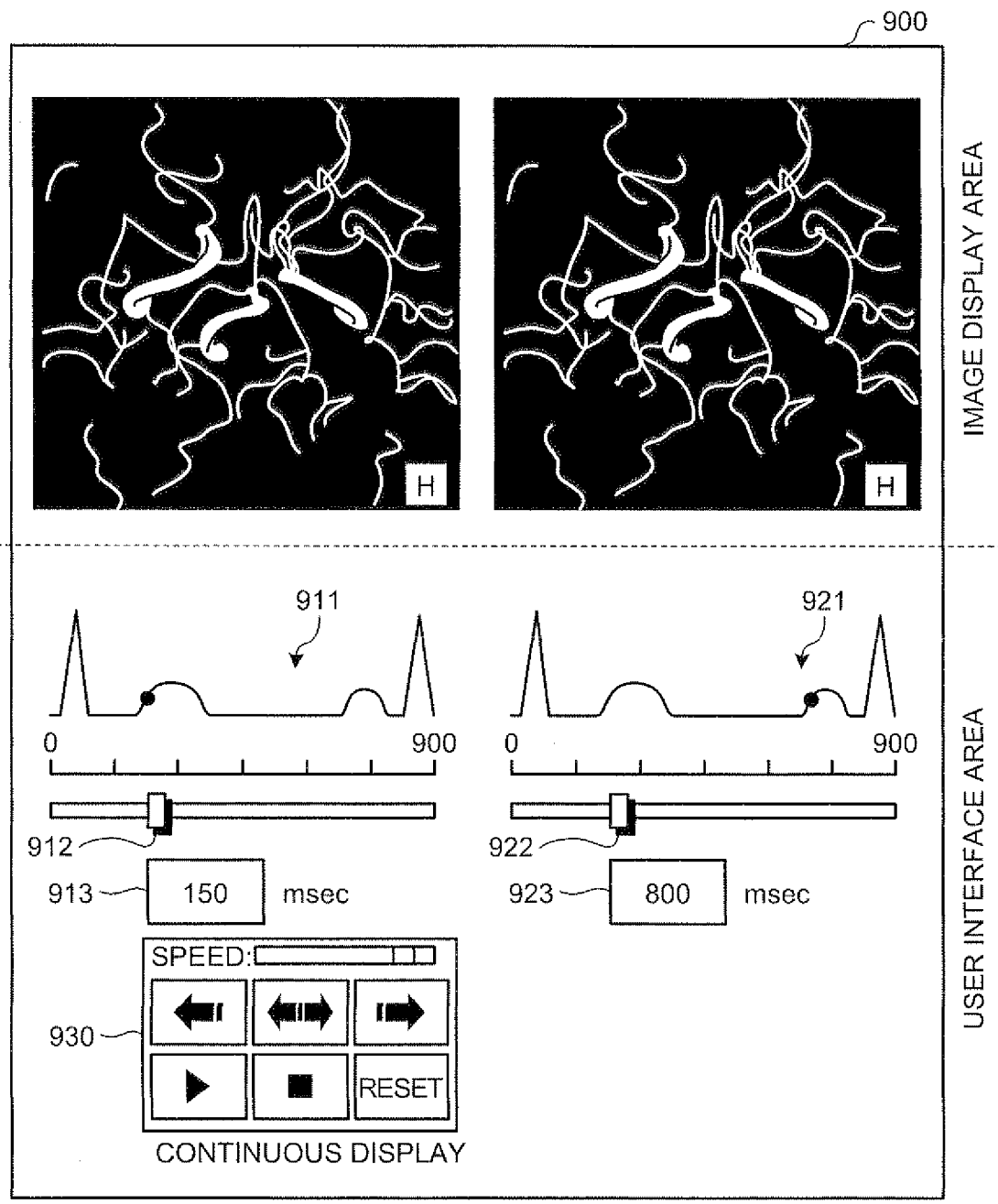
FIG. 16 is a schematic diagram illustrating an example of an image viewing screen when displaying three-dimensional images created by Maximum Intensity Projection (MIP) according a seventh embodiment of the present invention.
Figure 17:
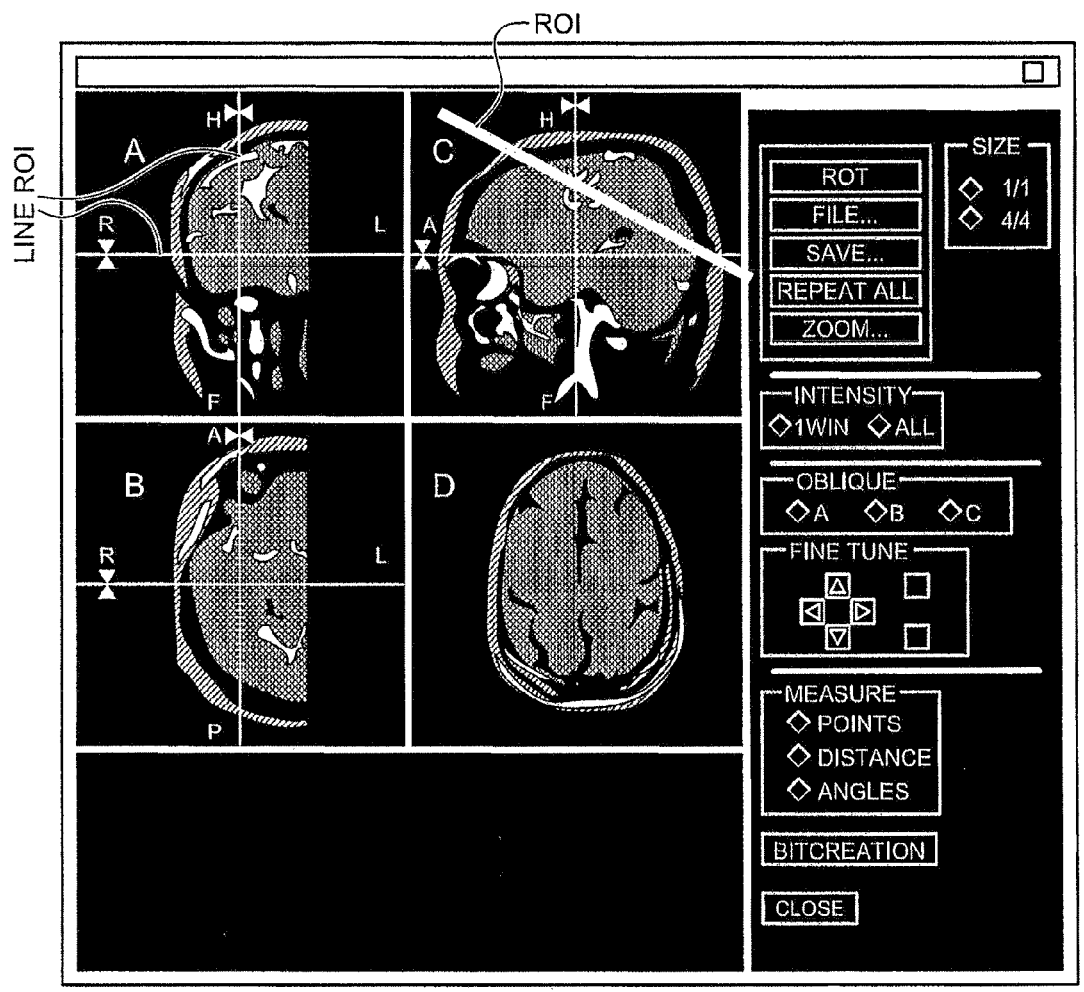
FIG. 17 is a schematic diagram illustrating an example of a Multi Planar Reconstruction (MPR) screen according to a conventional diagnostic imaging apparatus.

Although the above embodiments are explained in cases where two-dimensional (2D) images, such as MPR image data and cine image data, are displayed in the image display area; a three-dimensional (3D) image created by MIP can be displayed, for example. A case of displaying a three-dimensional image created by MIP is explained below as a seventh embodiment of the present invention. FIG. 16 is a schematic diagram that depicts an example of an image viewing screen when displaying three-dimensional images created by MIP.

As shown in FIG. 16, in this case, an image viewing screen 900 includes, for example, an image display area for displaying 3D images, and a user interface area for receiving input information about cardiac time phase.

In the image display area, for example, two images taken through a 3D scan of blood vessels in a head according to the Time Of Flight, and created by MIP (hereinafter, "MIP image") are displayed. The left and right images are images that are reconstructed by using data collected in time phases corresponding to a systole and a diastole of the heart, respectively. The MIP images displayed in the image display area can be observed from multiple directions as the images are displayed by being turned synchronously or separately.

Such images can be obtained through two scans by using ECG-gated imaging in combination, or can be collected through one scan according to a known method as disclosed in U.S. Pat. No. 6,505,064. Clinical meaning of the example is to capture change in diameter and form of not-ruptured aneurysma in cardiac cycle as disclosed in a non-patent document "Ningen Dock Vol. 21, No. 4, 2006, pp. 30-35".

On the other hand, in the user interface area, similarly to the image viewing screen 100 shown in FIG. 2, electrocardiographic waveforms 911 and 921 (including scale), sliders 912 and 922 and input boxes 913 and 923 for specifying a cardiac time phase, and a continuous display panel 930 for operating continuous display of images are displayed. By using the interfaces, the operator can perform image selection and animation display in accordance with a cardiac time phase.

Although according to the example shown in FIG. 16, two images are simultaneously displayed to compare images of two time phases, the number of images can be one, or three or more, depending on a purpose. Although the three-dimensional display described according to the sixth embodiment uses MIP, 3D images created by other three-dimensional display methods, such as volume rendering or surface rendering can be used.

The seventh embodiment is explained below with reference to FIG. 4. When the operator specifies a time phase by operating the slider 912 or 922, or inputting a numerical value into the input box 913 or 923 via the input unit 16, the control unit 17 selects the image data 14*c* of the specified time phase, creates the MIP image data 14*h* in a projection direction specified by the operator via the input unit 16 based on the image data 14*c* that is selected, and outputs the created image data together with the electrocardiogram data 14*b* to the display unit 15. Moreover, when the operator changes the time phase or the projection direction, the control unit 17 performs selection of a corresponding piece of the image data 14*c* and MIP processing in accordance with an instruction of the change, and outputs the MIP image data 14*h* to the display unit 15.

As described above, according to the seventh embodiment, the storage unit 14 stores therein image data in a manner associated with three spatial dimensions and time. The input receiving unit 17*a* displays 3D images, and receives input information about space and cardiac time phase. When the input receiving unit 17*a* receives input information about space and cardiac time phase, the screen-display control unit 17*b* then reads image data corresponding the dimensions of the received information from image data stored by the storage unit 14, and displays 3D images based on the read image data, so that the operator can efficiently observe the images by associating them with three spatial dimensions and two or more other dimensions.

The exemplary embodiments according to the present invention have been explained above. The above embodiments are explained in cases where the present invention is applied to an MRI apparatus; however, the present invention is not limited to this, and can be similarly applied to other diagnostic imaging apparatuses, such as an X-ray CT apparatus or a Positron Emission Tomography (PET) apparatus.

The components of each device shown in the drawings in the above embodiments are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated per arbitrary unit depending on various loads and conditions of the use.

For example, the present invention can be similarly applied to an image display system that includes an image server device that stores therein various image data and a client device that displays image data, the image server device being connected to the client device via a network (for example, Picture Archiving and Communication System (PACS)).

In such case, the image server device stores therein image data taken by a diagnostic imaging apparatus, such as an MRI apparatus or an X-ray CT apparatus, and the client device acquires image data from the server device and displays the acquired image data, receives input of a value about at least one element among multi-dimensional elements included in the image data, and displays image data corresponding to the received value.

As described above, the image display apparatus and the magnetic resonance imaging apparatus according to the embodiments of the present invention are useful for displaying images of various dimensions, and suitable particularly when observing images associated with multiple dimensions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus having a graphical user interface, said apparatus comprising:
 a storage unit storing a plurality of image data having multi-spatial dimensions for a scanned region of a subject;
 an analysis processing unit configured to generate a plurality of analysis results by performing predetermined analysis processing on said plurality of image data stored in the storage unit, said generated analysis results including at least one analysis result parameter respectively corresponding to each of said image data;
 a display unit configured to display said multi-spatial dimension image data stored in the storage unit together with a depiction of said at least one parameter; and
 an image-display control unit configured to cause multi-spatial dimension image data corresponding to at least one specified parameter analysis result to be displayed on the display unit when said at least one parameter analysis result is specified by an operator from among a plurality of possible said parameter values displayed by the display unit.

2. The apparatus according to claim 1, further comprising a Multi Planar Reconstruction (MPR) processing unit configured to generate an MPR image by performing cross-section conversion processing on said multi-spatial dimension image data stored in the storage unit, and wherein:
the storage unit stores multi-time phase volume data with respect to the scanned region of the subject,
the analysis processing unit is configured to generate multi-time phase analysis results by analyzing the multi-time phase volume data stored in the storage unit,
the display unit is configured to display an MPR image generated by the MPR processing unit and to display the multi-time phase analysis results generated by the analysis processing unit, and
the image-display control unit is configured to cause display of an MPR image corresponding to an operator specified multi-time phase analysis result when at least one multi-time phase analysis result is specified by an operator from among a plurality of multi-time phase analysis results displayed.

3. The apparatus according to claim 1, wherein the analysis processing unit is configured to generate sequential variations in a left ventricular volume of a heart of the subject, as the non spatial parameter value analysis results.

4. The apparatus according to claim 2, wherein the analysis processing unit is configured to generate sequential variations in a left ventricular volume of a heart of the subject, as the parameter value analysis results.

5. The apparatus according to claim 1, wherein the analysis processing unit is configured to generate sequential variations in myocardial wall thickness, cardiac output, or ejection fraction, of the heart of the subject, as the parameter value analysis results.

6. The apparatus according to claim 2, wherein the analysis processing unit is configured to generate sequential variations in myocardial wall thickness, cardiac output, or ejection fraction, of the heart of the subject, as the parameter value analysis results.

7. The apparatus according to claim 1, wherein the analysis processing unit is configured to generate a dynamic curve indicating sequential variations in the scanned region of the subject, as the parameter value analysis results.

8. The apparatus according to claim 2, wherein the analysis processing unit is configured to generate a dynamic curve indicating sequential variations in values of a pixel in the scanned region of the subject, as the parameter value analysis results.

9. The apparatus according to claim 1, wherein the analysis processing unit is configured to generate a flow-velocity curve indicating sequential variations in a flow velocity of nuclear magnetic response spin in the scanned region of the subject, as the parameter value analysis results.

10. The apparatus according to claim 2, wherein the analysis processing unit is configured to generate a flow-velocity curve indicating sequential variations in a flow velocity of nuclear magnetic resonance spin in the scanned region of the subject, as the parameter value analysis results.

11. The apparatus according to claim 1, wherein the analysis processing unit is configured to generate a Bull's eye image that depicts the parameter value analysis results in development elevation.

12. The apparatus according to claim 2, wherein the analysis processing unit is configured to generate a Bull's eye image that depicts the parameter value analysis results in development elevation.

13. The apparatus according to claim 3, wherein the analysis processing unit is configured to generate a Bull's eye image that depicts the parameter value analysis results in development elevation.

14. The apparatus according to claim 5, wherein the analysis processing unit is configured to generate a Bull's eye image that depicts the parameter value analysis results in development elevation.

15. The apparatus according to claim 7, wherein the analysis processing unit is configured to generate a Bull's eye image that depicts the parameter value analysis results in development elevation.

16. An image display apparatus having a graphical user interface, said apparatus comprising:
a storage unit storing a plurality of multi-spatial dimension image data for a scanned region of a subject that was obtained using respectively associated predetermined scanning parameter values;
a display unit configured to selectively display said image data as a function of a parameter value also displayed with the image data;
an input receiving unit configured to receive an operator input value of a predetermined scanning parameter; and
an image-display control unit configured to read and display image data corresponding to the input parameter value.

17. The apparatus according to claim 16, wherein:
the image data is obtained by a magnetic resonance imaging (MRI) apparatus, and
the scanning parameter is an MRI echo time.

18. The apparatus according to claim 16, wherein:
the image data is obtained by a magnetic resonance imaging (MRI) apparatus, and
the predetermined scanning parameter is a b value indicating strength of a Motion Probing Gradient (MPG) pulse used in an MRI scan for a diffusion emphasized image.

19. The apparatus according to claim 16, wherein:
the image data is image data obtained through a scan performed by a magnetic resonance imaging (MRI) apparatus, and
the predetermined scanning parameter is an MRI inversion time indicating a period from application of an inversion pulse to a start of an MRI scan using an inversion recovery method.

20. The apparatus according to claim 16, wherein:
the image data is obtained by a magnetic resonance imaging (MRI) apparatus, and
the predetermined scanning parameter is a delay time period from occurrence of a trigger waveform to start of an MRI scan during one of (a) electrocardiogram (ECG) gated imaging and (b) pulse-wave synchronized imaging.

21. The apparatus according to claim 16, wherein:
the image data is obtained by a magnetic resonance imaging (MRI) apparatus, and
the predetermined scanning parameter is an inversion time period from application of an inversion pulse to start of an MRI scan during angiography without contrast agent, where blood flow dynamic states in the scanned region are imaged by labeling a specific region in the region by applying the inversion pulse to the specific region.

22. An image display apparatus having a graphical user interface, said apparatus comprising:

a storage unit storing multi-spatial dimension image data that is reconstructed with respect to each of plural cardiac time phases based on data collected across a plurality of heart beats;

a display unit configured to selectively display said image data stored in the storage unit and to display a representation of an electrocardiographic waveform of one heart beat; and an image-display control unit configured to read image data corresponding to a user-specified cardiac time phase when a displayed cardiac time phase on the electrocardiographic waveform is specified by the user, and to cause display of the thus read image data.

23. The apparatus according to claim 22, wherein the electrocardiographic waveform is a simulation diagram that depicts a typical electrocardiographic waveform.

24. The apparatus according to claim 22, wherein the electrocardiographic waveform is one electrocardiographic waveform of heart beats from among a plurality of electrocardiographic waveforms of heart beats measured from the subject during a scan.

25. A magnetic resonance imaging apparatus having a graphical user interface, said apparatus comprising:

a storage unit storing multi-spatial dimension image data that is reconstructed with respect to each of plural cardiac time phases based on data collected across a plurality of heart beats;

a display unit configured to display image data stored in the storage unit and to display a representation of an electrocardiographic waveform of one heart beat; and an image-display control unit configured to read image data corresponding to a user-specified cardiac time phase when a cardiac time phase displayed on the electrocardiographic waveform is specified by the user, and to cause the display unit to display the thus read image data.

* * * * *